United States Patent [19]

Junker et al.

[11] Patent Number: 4,763,274

[45] Date of Patent: Aug. 9, 1988

[54] MACHINE IMPLEMENTED ANALYSIS EDDY CURRENT DATA

[75] Inventors: Warren R. Junker, Monroeville; George A. Savage, Belle Vernon; Ronald H. Ingraham, Swissvale; David A. Bone, Penn Hills; Mustan Attaar; Raymond P. Castner, both of Monroeville; Bruce J. Taszarek, Mt. Lebanon, all of Pa.

[73] Assignee: Westinghouse Electric Corp., Pittsburgh, Pa.

[21] Appl. No.: 878,095

[22] Filed: Jun. 24, 1986

[51] Int. Cl.$^4$ ............................................. G01R 33/12
[52] U.S. Cl. ................................. 364/481; 364/551; 324/220; 324/238; 324/83 Q
[58] Field of Search ............... 364/481, 483, 484, 508, 364/551, 552, 580, 507; 324/223, 228, 229, 238, 83 Q, 220

[56] References Cited

U.S. PATENT DOCUMENTS

| | | | |
|---|---|---|---|
| 3,693,075 | 9/1972 | Förster | 324/229 |
| 4,194,149 | 3/1980 | Holt et al. | 324/238 |
| 4,207,520 | 6/1980 | Flora et al. | 324/238 |
| 4,631,688 | 12/1986 | Boehm et al. | 364/481 |
| 4,663,727 | 5/1987 | Saporito et al. | 364/552 |

OTHER PUBLICATIONS

Shankar et al., "Feasibility of Using Adaptive Learning Networks for Eddy Current Signal Analysis," EPRI Report NP-723, Mar. 1978.

Deeds, et al., "Determination of Multiple Properties with Multiple Eddy-Current Measurements", International Advances in Nondestructive Testing, 1981, vol. 8, pp. 317–333.

Primary Examiner—Parshotam S. Lall
Assistant Examiner—V. N. Trans
Attorney, Agent, or Firm—D. C. Abeles

[57] ABSTRACT

A digital computer performs a complete eddy current analysis of the tubes of a steam generator from data input to generation of a final report. The computer extracts signatures generated by various structural features and tube defects from the data, breaks down composite signatures into their component parts and classifies each such signature by applying thereto a cascading set of experience based rules. Signatures classified as structural features are examined closely for the presence of colocated tube defects. A post processor correlates the location of the indication identified from the time based eddy current data with the known physical location of the structural features so that the position of the defects can be presented in terms of distances from fixed structures.

38 Claims, 16 Drawing Sheets

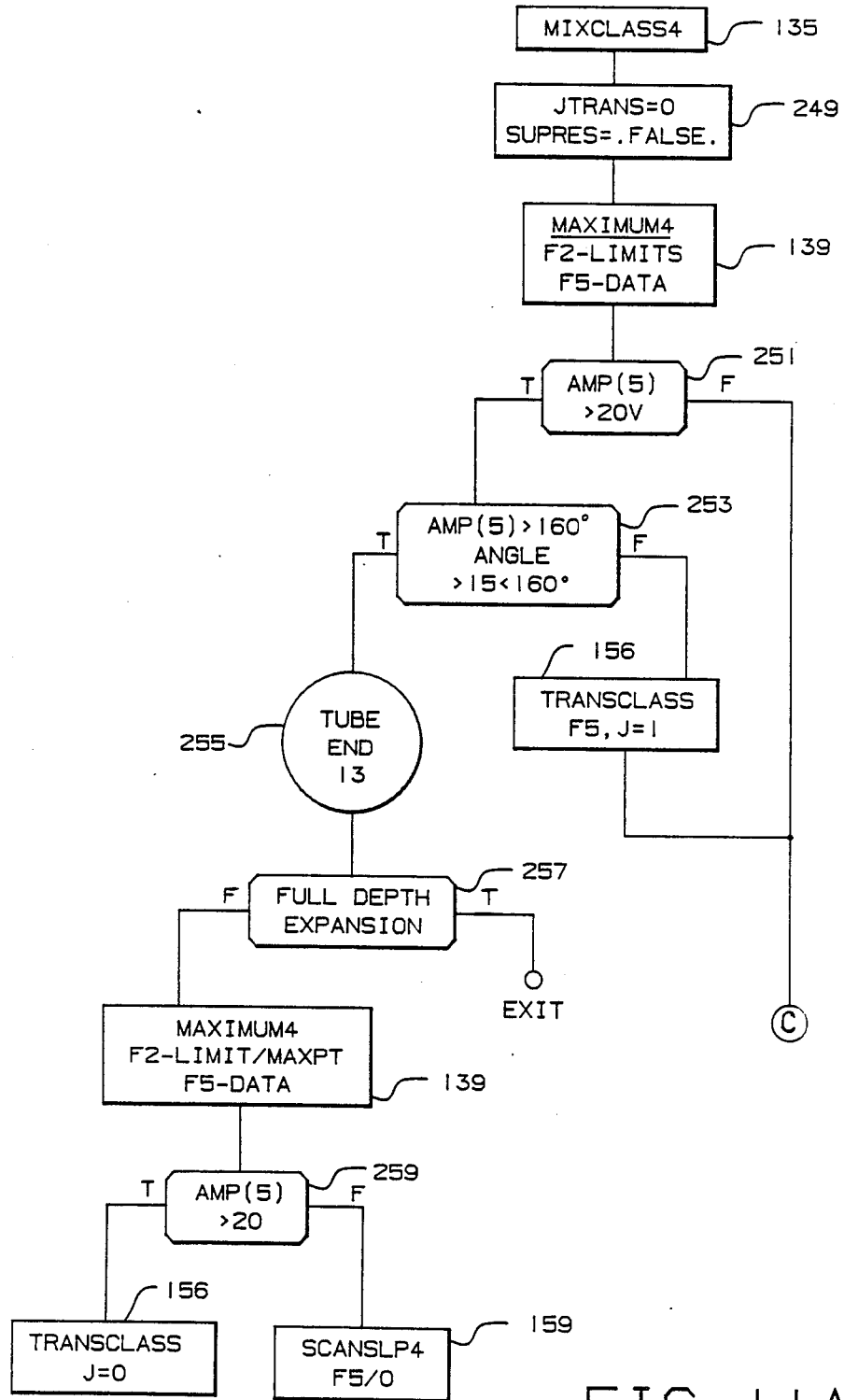
FIG. IIA.

MACHINE IMPLEMENTED ANALYSIS EDDY CURRENT DATA

FIELD OF INVENTION

This invention relates to a method and apparatus for using a programmed digital computer to analyze eddy current data generated in nondestructive testing of electromagnetically active objects, and more particularly to such a method and apparatus for automatically detecting flaws in the heat transfer tubes of a heat exchanger such as those used in the steam generator of a nuclear steam supply system using rules of interpretation supplied by an expert human analyst.

BACKGROUND INFORMATION

Eddy current testing is a commonly used method of nondestructive testing of metallic objects. In one type of system widely used in such testing, the change in impedance of an active electrical coil as it is passed in close proximity to the test object is used to detect flaws. Any variations in the shape or other characteristics of the test object, not just flaws, produce changes in the eddy current signal. For instance, in testing the tubes in a steam generator of a nuclear steam supply system the massive steel tube sheet in which the ends of the U-shaped tubes are mounted, the metal support plates and antivibration bars which support the intermediate portions of the tubes and even deposits which form on these components, produce variations in the eddy current signals. In addition, wobble of the probe as it passes through the tube generates responses which act as noise in the data. Furthermore, there are various geometries of discontinuities such as cracks, pits, dents and thinning of the tube wall thickness which have different effects on the eddy current signal.

The difficulty with eddy current testing is that it does not produce a clear, easily recognizable representative of the characteristics of a test object, such as for instance, an X-ray picture would provide. In addition, a flaw may occur adjacent to a known feature such as a support plate in the case of the steam generator, and thus its response could be masked by the larger signal. As a result, eddy current analysis of steam generator tubes is performed by a small cadre of vigorously trained, extremely skilled analysts who over a period of time have collected a large-body of "experience based" knowledge.

In performing an eddy current test on steam generator tubes a probe is advanced through the tube and the signals so generated are recorded for later analysis. Tests are made at several frequencies, and in some cases signals at various frequencies are "mixed" in a manner which eliminates selected signals, such as those produced by the support plates, so that signals related to flaws at those locations may be extracted from the data. Most of the data are taken with a differential coil pair which produces signals of the opposite sense as each coil successively passes the same tube feature, although an "absolute" coil which is a single coil paired with a reference coil is also used.

For analyzing the data, the human analyst selects whatever frequency he desires for presentation on a cathode ray tube display. The display includes a strip chart presenting the real and imaginary (quadrature) components of the recorded signal for the entire length of the tube under examination. At the analyst's request; any portion of the strip chart can be displayed simultaneously in the form of a lissajous pattern. A lissajous pattern is a well known display in which the real and imaginary components for successive points in the data are plotted in an X-Y plane. Such a plot forms lobes radiating from an origin with the angular position of the lobe representing the phase angle. The human analysts have developed a highly refined ability to observe the shape and phase angle of the lissajous pattern and determine therefrom with a good deal of confidence the characteristics of the tube represented by that pattern. It should be appreciated that for the most part the lissajous patterns are not perfect geometric figures which adds to the difficulty of interpretation. In order to classify a characteristic, the human analyst may switch to other channels to observe the corresponding portion of the signal. In performing an analysis, the human analyst is capable of recognizing, through experience, the pertinent characteristics of the lissajous figures which indicate critical features while rejecting extraneous indications.

The routine nondestructive eddy current inspection of steam generator tubes has become increasingly important and complex as the need to extract more information from the inspection results has increased. During the past decade several factors have contributed to the transformation of a simple maintenance requirement into one of the most critical tasks of the plant outage. Increasingly the NRC, as well as the plant owner/operator need maximum information on the condition of the tubes in the steam generator. The new breed of digital eddy current instruments and multiple sensor probes can now provide a massive volume of inspection data. The tooling to place the probes in the tubes to collect this data has also become very efficient. Thus the number of tubes interrogated, the number of test variables used, and the number of tubing degradation mechanisms have all increased significantly, but the speed of formulating a meaningful interpretation from this information has lagged behind. The already demanding working conditions of human analysts are exacerbated by the fact that the eddy current inspection is usually on the critical path of the utility's outage schedule.

In an effort to provide more information for plant life extension, the number of tubes inspected at every outage has gradually increased. Recently it has not been unusual to find 100% inspections of the 3000 to 5000 tubes in a typical steam generator while a statistical 5%–10% inspection was considered satisfactory in the past. The data is used not only to establish whether the degradation of the tube or loss of the tube wall exceeds 40%, a level requiring remedial action such as sleeving or plugging, but to monitor (and predict) the various mechanisms of degradation. This information is used to take steps to arrest the degradation mechanism. All of these requirements have placed a large burden on the resources of a single data analyst. As a result, procedures have been established in which a secondary and sometimes even a tertiary review of the same data by independent data analysts has been used in order to increase the level of confidence and divide the process into manageable tasks.

SUMMARY OF THE INVENTION

In accordance with the invention, a programmed digital computer is used to perform a complete analysis of heat exchanger tube eddy current data from data input to an edited report to be delivered to the customer. The difficulty with such machine implemented analysis is that the digital computer can only examine the data point by point. Before the expert rules of analysis developed by the human analyst can be applied by the computer, it must first construct the signatures which can then be examined to determine whether they represent structural features, such as, for instance, tube ends, tube sheets, tube supports, and antivibration bars; tube defects such as, for instance, flaws and dents; or irrelevant features, such as noise or residuals from mixing frequencies et cetera.

The signatures are constructed by operating the computer to compare the data which is recorded in quadrature in several frequencies, in both the differential and absolute modes, with threshold values. The threshold is a noise circle in the X-Y plane of the quadrature components centered on a weighted moving average value of the eddy current signal. Since the noise tends to be unidirectional, different factors are applied to the X and Y components of the data before comparing it with the noise circle which effectively converts the noise circle to an ellipse while maintaining the ease of adjusting the location of the noise circle for drift by moving its origin.

Lobes are identified by the computer by the point at which the data exits the noise circle and the point at which it returns. Lobes within a preselected number of data points of each other are grouped together into a signature. A signal which remains out of the noise circle for more than a preselected number of data points, for instance a number of data points representative of about six inches along the tube, probably is made up of a number of composite signatures representative of more than one feature. Segments of such elongated signatures in which there is no overlap between components in designated frequencies are broken down into component signatures by phase angle. In the preferred embodiment of the invention, the computer successively selects a base lobe in the elongated signature and groups all lobes with a phase angle within a preselected number of degrees of the phase angle of the base lobe into a component signature.

Segments of the elongated signatures in which there is overlap between components in the designated frequencies are broken down by dividing the overlapping portions in one frequency into smaller segments and identifying those segments as component signatures. Since the length of the segments sliced off of the overlapping portions of the signature are of arbitrary length, the computer makes sure that a component signature is not split by adjusting the end of a segment which occurs within a preselected number of data points of the maximum amplitude of the segment. The overlapped segments of other frequencies are then broken down into component signatures by phase angle if necessary before analysis as individual signatures.

Once the computer has identified signatures in all the frequencies, it applies a cascading set of rules based upon the experience of expert analysts to classify each of the signatures as one of the selected group of structural features, tube defects or irrelevant signals.

The larger amplitude signals which most likely represent the structural features such as tube ends, support plates, tube sheets, antivibration bars and transition areas where tubes are expanded in the tube sheet are analyzed first. Since flaws often occur in the vicinity of these structural features, these larger signals are then examined further to determine if they also contain flaw signals. The computer looks for small lobes on the larger signal which may represent flaws. It does this by constructing piece by piece from these signatures, segments over which the rate of change of the amplitude of the data does not change by more than a threshold value. In the exemplary system, two different techniques are used to accomplish this. In one, straight line segments are drawn between data points and successive segments having phase angles within a selected number of degrees of each other are grouped into extended segments which are then examined for flaw like characteristics. In the second technique, triangles are formed between successive groups of three data points and the data points associated with successive triangles having an area less than a threshold value are grouped into the extended segments which are examined for flaw like characteristics.

In order to reduce the work load of the computer, the portions of the signature representing structural features which are examined for colocated flaws is reduced such as by limiting the search in the frequency most conducive to detecting flaws to the data point limits of the corresponding signature in another frequency. In other instances, the search is confined to a selected number of data points from the maximum amplitude point of the signature.

Once the computer has classified all of the signatures, a correlation is made between the locations of the identified features as determined from the time based eddy current data and the known physical location of the support structures so that the position of the flaws can be reported in terms of distances from these permanent structures.

While the analysis is performed completely by the computer without the need for human intervention, the preliminary findings are made available to a human analyst for review, and modification if desired, both in printed and graphical formats. In the graphical mode, strip charts of the full length of the tube for a selected X channel and Y channel for any frequency, not necessarily the same frequency, zoom X and Y channel strip charts of any selected portion of the tube for any frequency and lissajous patterns of the selected portion for five frequencies are presented simultaneously. A hard copy of the display can be generated by a graphics printer.

Aspects of the invention have broad application to machine implemented analysis of eddy current data from other materials besides the tubes of a heat exchanger.

BRIEF DESCRIPTIONS OF THE DRAWINGS

A full understanding of the invention can be gained from the following specification when read in conjunction with the accompanying drawings in which.

Figure 7:
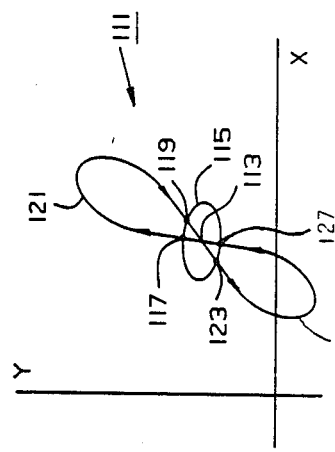
Figure 8A:
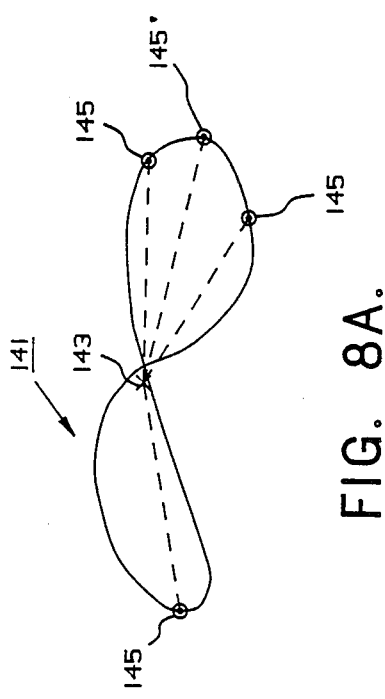
Figure 3:
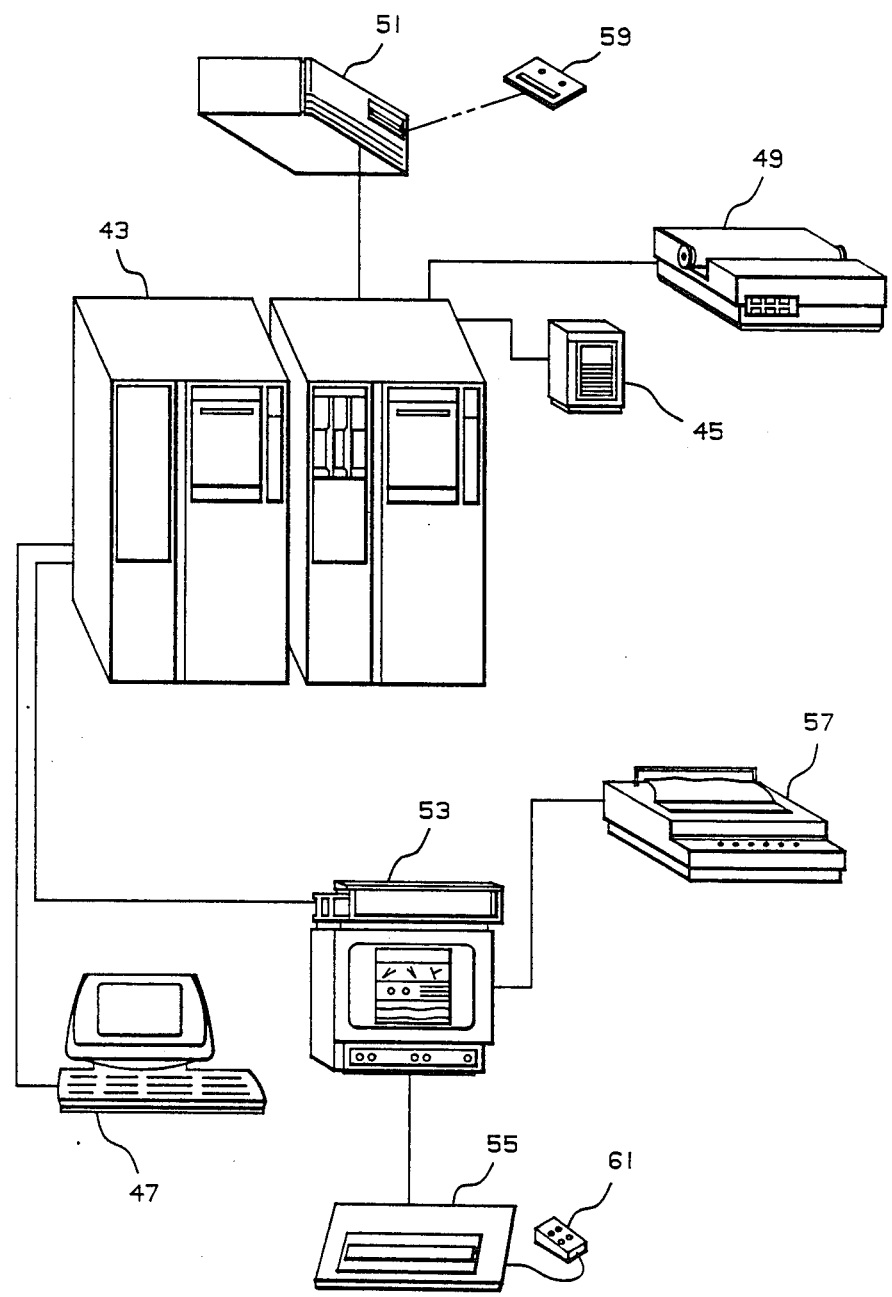
FIG. 3 is a schematic diagram of the major hardware components used in accordance with the invention to analyze eddy current data obtained with the probe of FIG. 2.
Figure 6A:
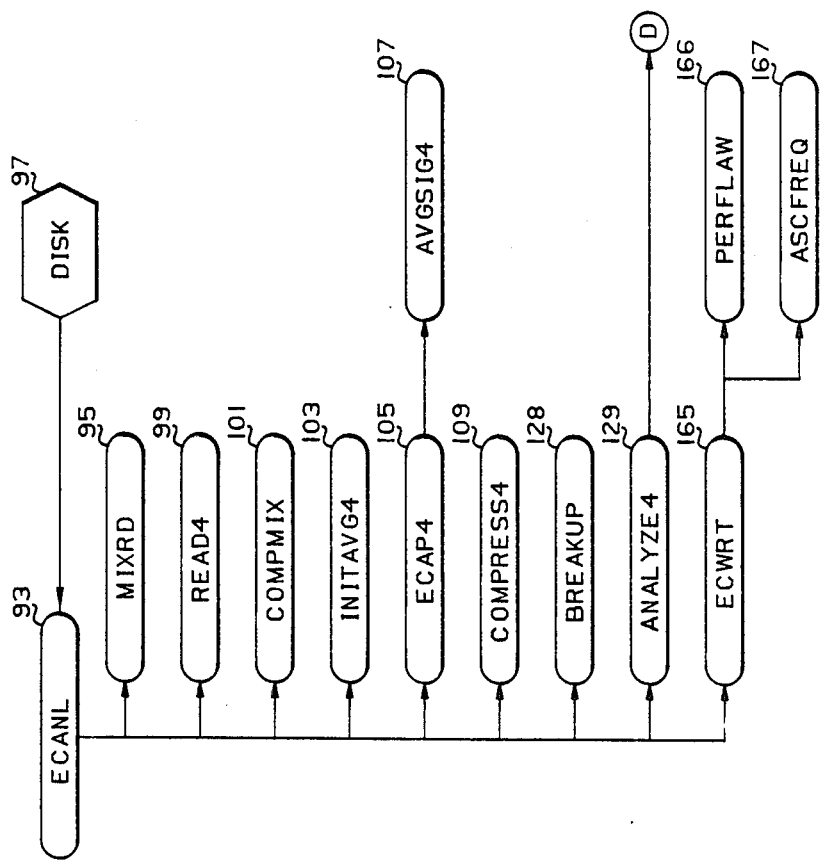
Figure 6B:
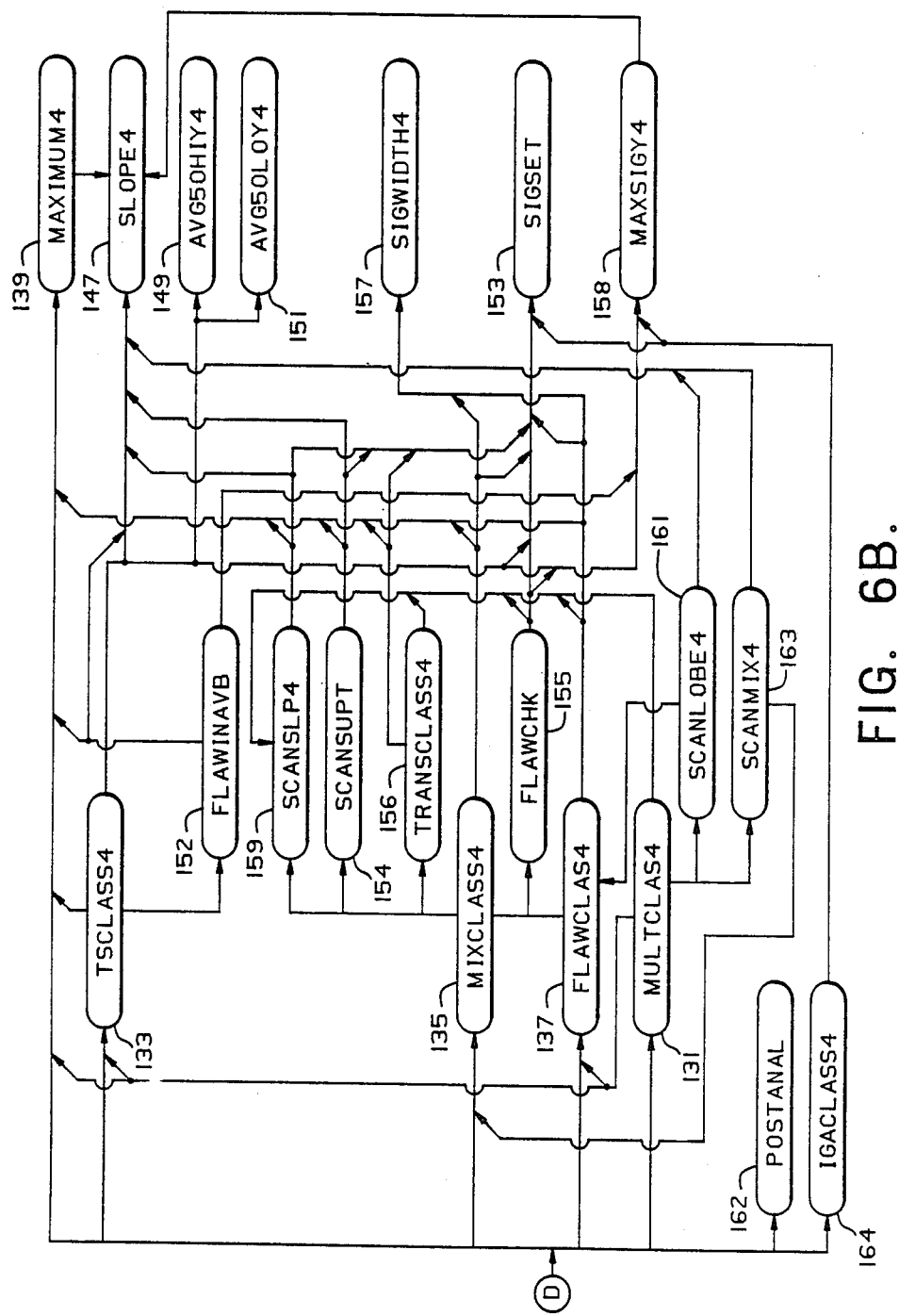
Figure 9:
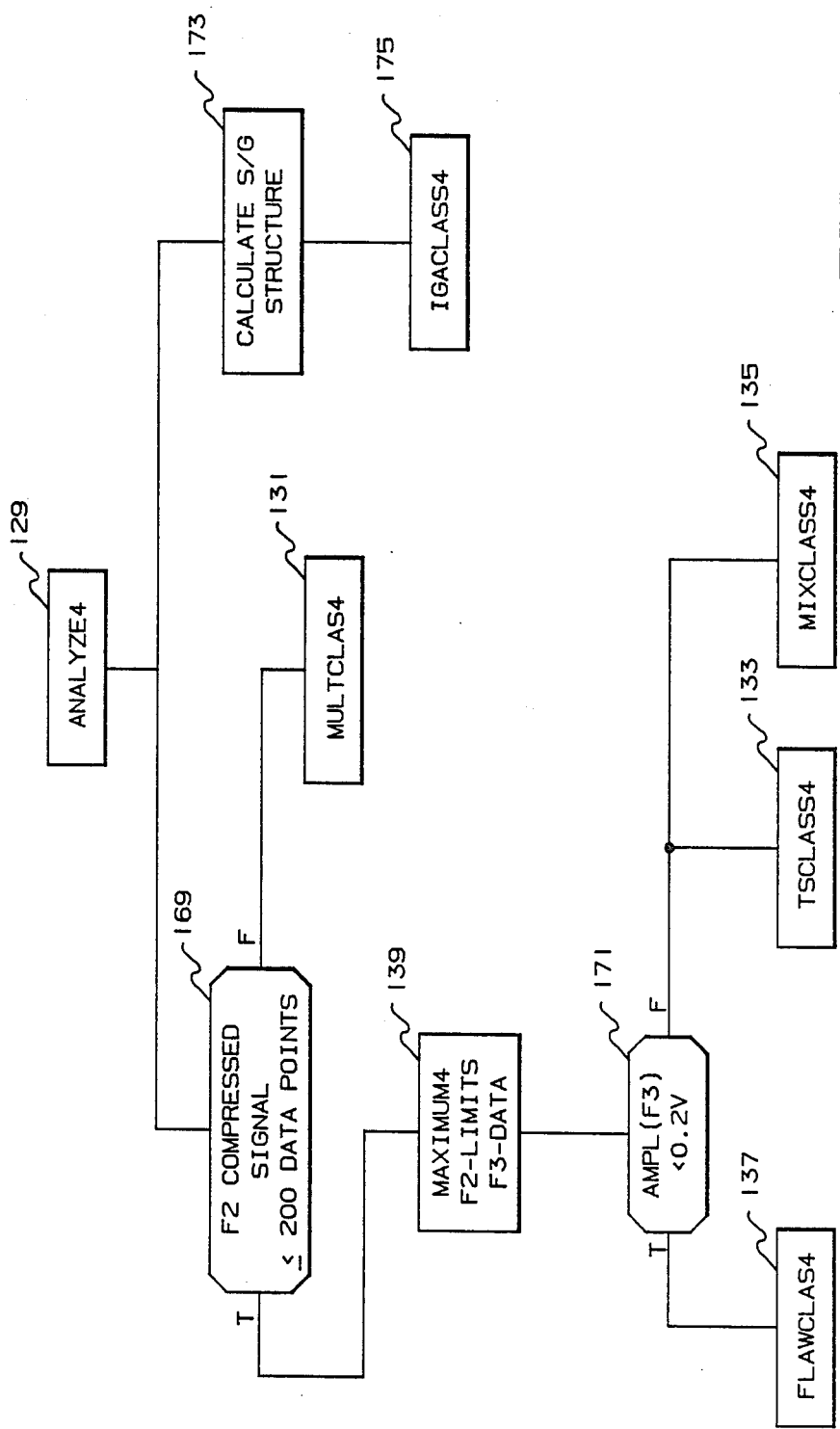
Figure 10A:
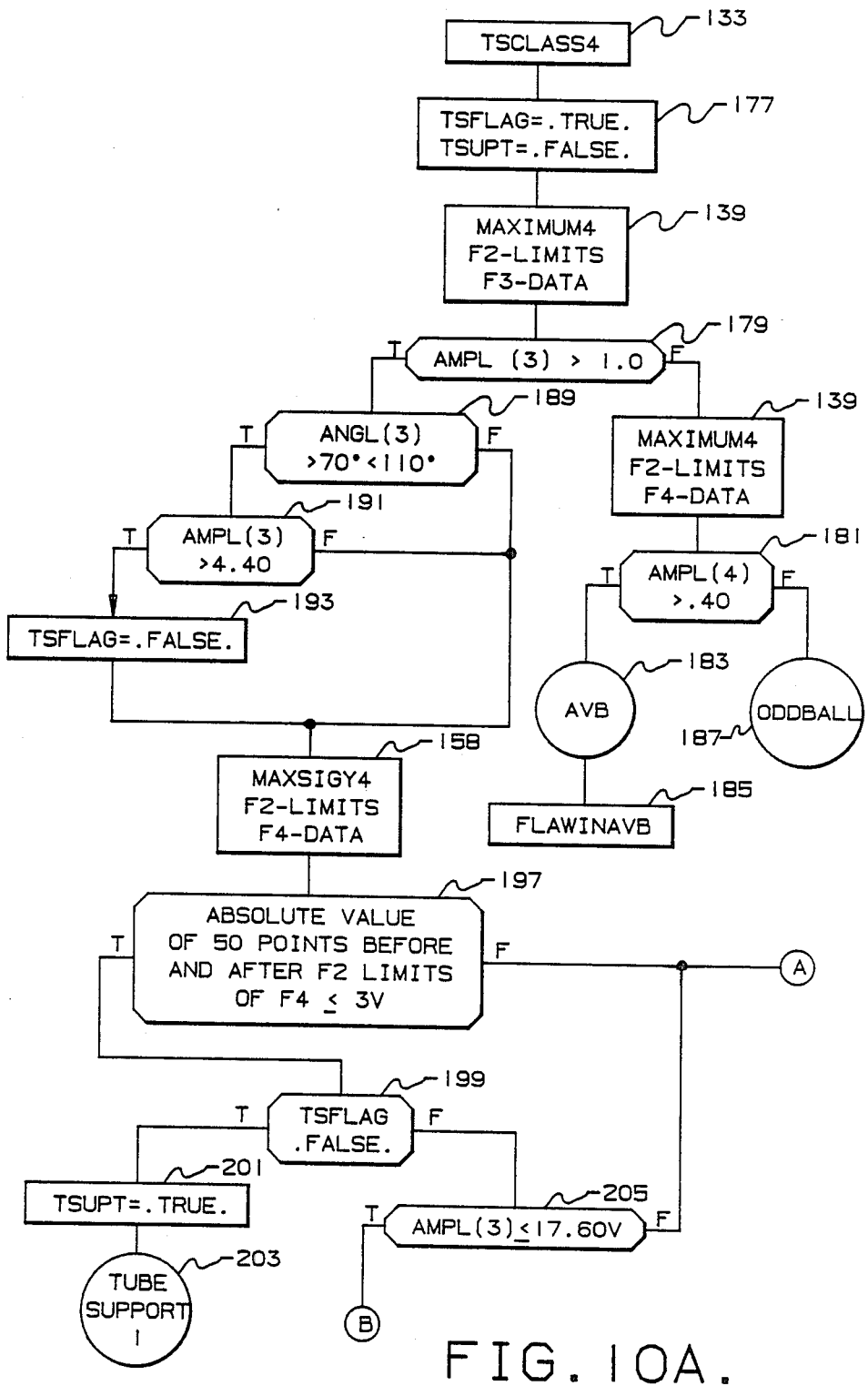

FIGS. 6a and b shown a block diagram illustrating the interaction of the subroutines of the program used by the digital computer which forms part of the hardware of FIG. 3;

FIG. 7 is an example of an X,Y plot of a lissajous figure illustrating the noise ellipse used by the subject invention;

FIGS. 8a and b illustrate graphically the scheme by which the invention determines the maximum amplitude of an eddy current signature; and FIGS. 9, 10a, b and c, 11a and b and 12 through 14 are flow diagrams of the major routines shown in FIG. 6.

DESCRIPTION OF THE PREFERRED EMBODIMENT

Figure 1:
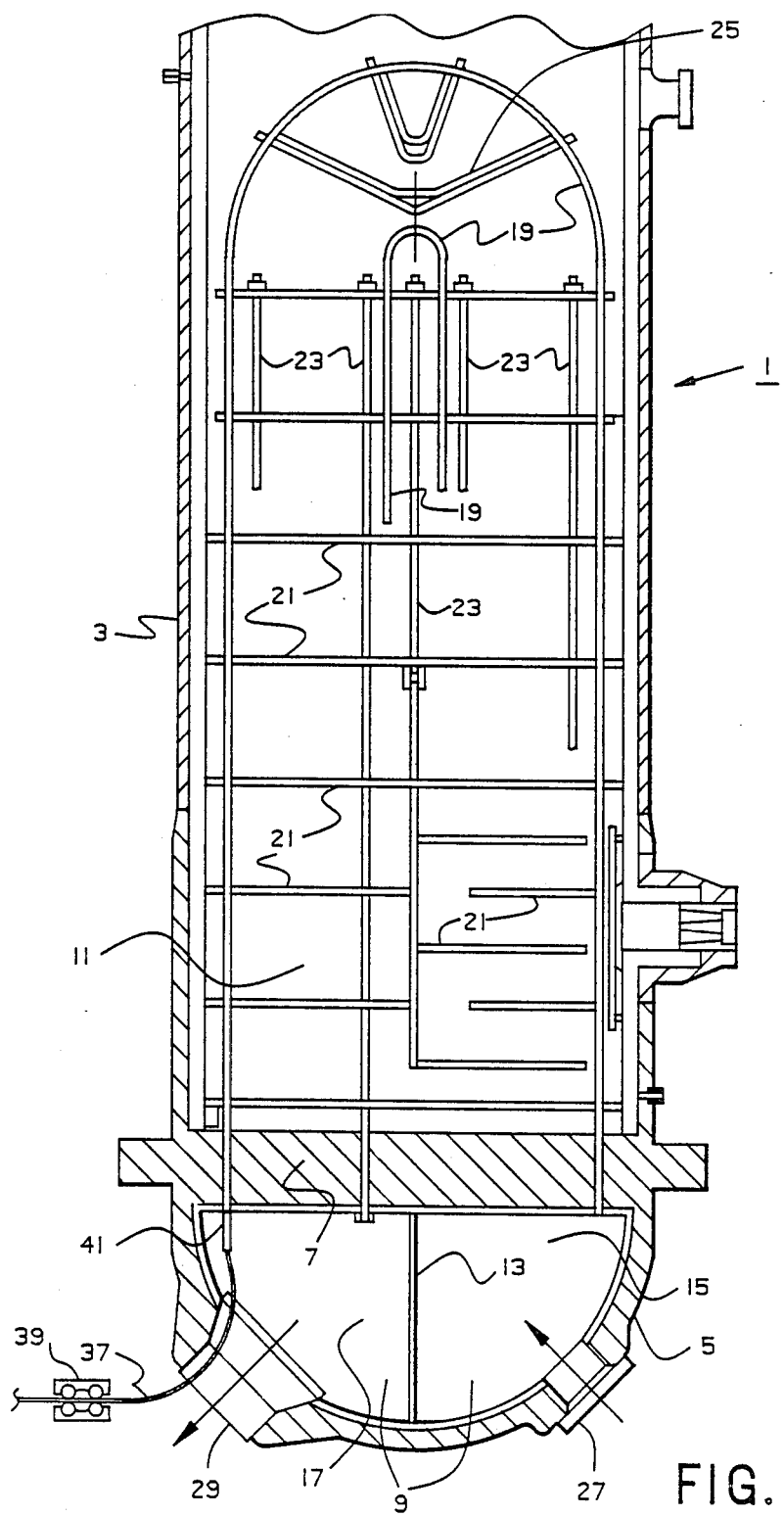
FIG. 1 is a vertical section through a typical steam generator with apparatus in place for recording eddy current data for use in the subject invention.

The invention will be described as applied to analysis of eddy current data generated from an inspection of the steam generator 1 shown in FIG. 1 which is a typical steam generator which forms part of the nuclear steam supply system in a pressurized water reactor electric power generating plant. The steam generator 1 comprises a cylindrical body portion 3 which is fitted at its lower end with a hemispherical shell 5. A transverse steel plate 7, called a tube sheet, at the lower end of the cylindrical portion divides the steam generator into a primary side 9 below the tube sheet and a secondary side 11 above. The primary side 9, which is also referred to as the channel head, is divided in half by a vertical divider plate 13 into an inlet section 15 and an outlet section 17. Thousands of U-shaped tubes 19 (only parts of 2 shown for clarity) are mounted in the secondary side 11 with one end extending through the tube sheet 7 into the inlet section 15 and the other into outlet section 17 of the channel head 9. The tubes 19 are supported on the secondary side 11 of the generator by a series of metal support plates 21 braced by tie rods 23, and by antivibration bars 25. Access can be gained to the tubes 19 through an inlet 27 and outlet 29 of the channel head.

Figure 2:
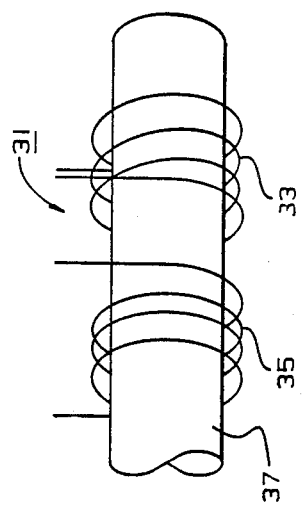
FIG. 2 is a schematic diagram of the probe used for obtaining eddy current data from the tubes of the steam generator shown in FIG. 1.

In performing an inspection of the tubes 19 of the steam generator 1, a probe 31 in the form of a pair of differentially wound coils 33 and 35, as schematically shown in FIG. 2, is mounted on the end of a long flexible non-electromagnetically active rod 37 which is inserted sequentially into each of the tubes to be inspected. As shown in FIG. 1, the rod 37 carrying the probe 31 is fed into the selected tube by a drive mechanism 39. As the rod 37 is withdrawn from the tube 19, the coils 33 and 35 are sequentially multiplexed typically at 400 KHz, 200 KHz, 100 KHz and 10 KHz. For the differential signals, measurements are taken from the oppositely wound coils 33 and 35 measured simultaneously. For the absolute signals, a measurement is taken from only one of the coils and this signal is compared with that generated in an external reference coil (not shown). Data is taken 400 times per second, that is, the sequence of 4 differential signals and 4 absolute signals is repeated every 2.5 milliseconds. The probe is withdrawn from the tube at a nominal speed of 1 foot per second so that the data points are about 0.03 inches apart.

As is well known in the field of eddy current testing, variations in the characteristics of the tubes such as dents, flaws such as pitting, cracks, and thinning, et cetera, of the walls, as well as the presence of adjacent structures such as the support plates 21, the tube sheet 7 and the antivibration bars 25, influence the effective impedance of the probe coils 33 and 35. The signals thus generated are recorded in quadrature, X and Y, components for later analysis. In order to calibrate the system, a test section of tube 41 is connected to the end of a selected tube 19 so that the probe must pass through the test section as well as the tube to be tested. The test section 41 is provided with standard flaws in the form of 20%, 40%, 60%, and 100% through wall holes of specified diameter, and a standard ring which surrounds the tube and generates an indication similar to that of a support plate 21. The signals generated by these test features are also recorded. Calibration information is taken each time the probe is changed, for each new reel of recorded data and periodically during the inspection. Data from 80 to 300 tubes, depending upon whether a full or only partial inspection is made, can be recorded on each reel.

What has been described to this point is the typical known manner of collecting the eddy current data. Under current practice, the recorded data is processed by a digital computer to generate a strip chart display of a selected frequency and a lissajous pattern of a portion of the signal as selected by the human analyst. The analyst makes the decision as to what parts of what signals are to be displayed, and makes a determination as to what those signals represent with regard to the physical characteristics of the tube being examined and the surrounding structure.

In accordance with the present invention, the entire analysis from data input and signal processing, through data analysis and printout of a final report, is carried out automatically, although provision is made for operator review, and override if appropriate.

General Description

The present system was conceived to provide a human data evaluator or analyst a more powerful analysis tool which harnesses the fast, tireless capabilities of computer technology to sift through large volumes of data. The implementation of this idea has evolved into a software program that emulates the thought process used by the human analyst. It applies a set of "expert" rules to accept or reject portions of the data stream as signals containing worthy information. Each selected portion of the data stream is further subjected to the same scrutiny by the computer that a human analyst applies using another set of "expert" rules to ascertain the cause of the signal and to classify the corresponding tube condition. It is designed to be used as a diagnostic tool to evaluate the present condition of steam generators and to predict potential areas of concern in the future operation of the steam generator.

The raw data consists of eddy current responses from the bobbin coils 33 and 35 in both the differential and absolute modes. A set of 4 frequencies is used by the standard methods employed in field inspections. Raw data from two or three of these 4 frequencies in the differential or absolute mode are further mixed using the computer to create another channel of "mixed" data. The mixing allows elimination of unwanted signals.

The process of evaluating the massive amount of data involves imposing a set a cascading rules on some primary channels of the data and correlating information from some of the other channels to reduce the volume of the data set that is examined in each successive step.

The selection of the "expert" rules and the methods of applying them constitute the heart of the system. The entire raw data set is first "conditioned" so that it has an enhanced signal to noise ratio, becomes easy to manipulate with the computer, receives appropriate labels so that subsequent human interaction becomes easier, and is aligned in proportion to present the lissajous "patterns" that are familiar to the human analyst. This "conditioning" phase lays the foundation for the next step of the in-depth analysis; the application of the set of "rules". As mentioned earlier, one or more mixed channels can be created using specially developed software by mixing 2 or more signal frequency "corresponding" data sets.

The set of rules is vast and complex. These rules interact at various levels in the program. To insure that no "indications" are missed, a decision to exclude portions of data from further scrutiny is iteratively subjected to "test". Considerable experience with processing various data sets has led to an optimum balance between the amount of checking and the loss of relevant information.

Once a segment of data set is determined to contain information of value, it is processed again using information obtained from the various frequencies used in inspection. The use of maximum available information (again based on eddy current technology and expertise) is only possible with a computer. Human analyst would be limited by time and the ability to retain corresponding sets of information on a repeated basis for 10 to 20 signals per tube and thousands of tubes per steam generator.

At this stage, the data set has been broken up into a set of discrete segments that contain signals which can be classified into different categories. This information alone is of considerable value to the plant operator and to the human data analyst. At this stage, the analyst may use the system output since his entire effort is reduced to a concentrated review of "significant" portions of the data set.

Each category (such as dent, flaw, tube support plate, antivibration bar, tube sheet, etc.) is then analyzed to discriminate within that category. For example, a set of rules is applied to correlate certain flaw signal parameters to previously calculated calibration curves and establish the size or depth of the flaw, and its most likely position. Another set of rules determines the degradation of tube support plates or the tube sheet. Another set of rules can be applied to distinguish external phenomena like copper or sludge deposits.

System Hardware

The major components of the system are illustrated in FIG. 3 and include a Data General MV4000 mini computer 43 with associated tape drive 45 and hard disk (internal), an operator's terminal 47, a dot matrix printer 49, a digital tape drive 51, a graphics terminal 53, a graphics tablet 55, and a graphics color printer 57.

All of the software routines including system control, data acquisition, data analysis and display/graphics software reside on the hard disk. The digital tape drive 51 is also controlled by the computer 43. It has the capability of accessing any particular tube of data from a 3M-16 track data cartridge tape 59. These tapes 59 contain data recorded in a specific format as defined by the field data acquisition system. Both analog and digital data tapes can be utilized.

The raw data and the analysis results can be viewed on the graphics display terminal 53 and the operator's display terminal 47 respectively. The images of raw data on the graphics display terminal 53 can be manipulated using the cursor (of the mouse 61) and the graphics tablet 55. The system provides reviewing of several different channels in lissajous and strip chart format as described below: The operator can view an entire tube of strip chart data for one X component and one Y component "quadrature components" of any of the frequencies of raw data or mixed data. Hard copies of the analysis output with calls requiring remedial action can be generated by the dot matrix printer 49. Also, color prints of selected indications on the graphics display terminal can be generated by the graphics color printer 57.

System Software

Figure 4:
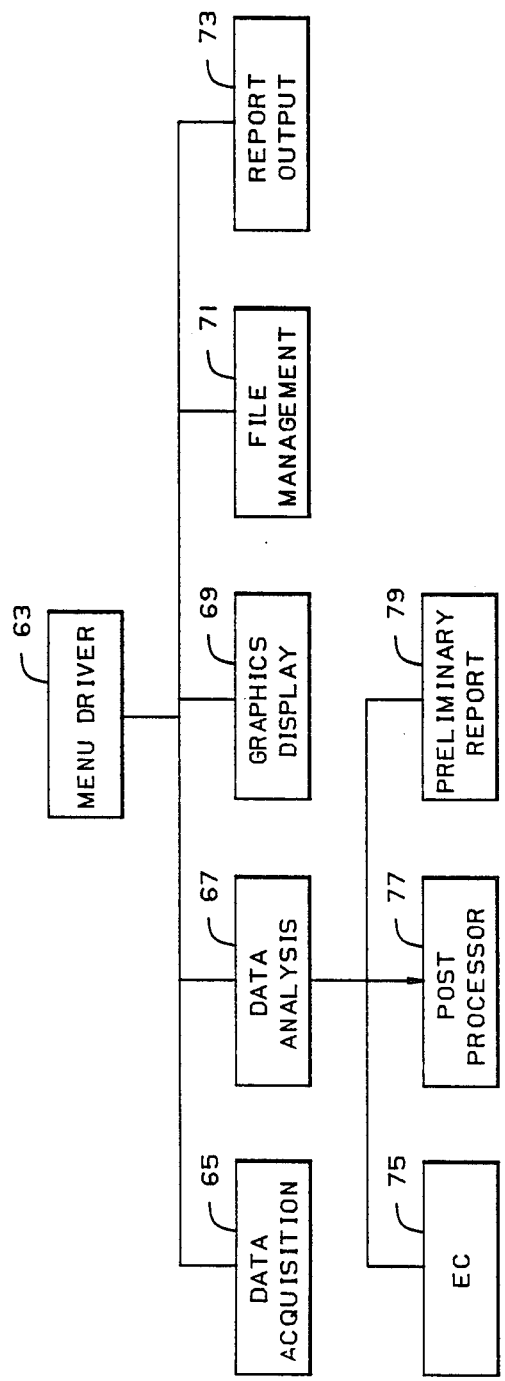
FIG. 4 is a block diagram of the overall structure of the software used in the apparatus of FIG. 3.

The overall structure of the software is illustrated in FIG. 4. It is designed to be menu-driven, interactive and operator friendly. The functions which can be selected through the menu driver 63 are data acquisition 65, data analysis 67, graphics display 69, file management 71 and report output 73. The data acquisition software 65 controls the operation of the digital tape recorder, advances a tape in the cassette to the correct block, recovers the data and accounts for variation in recorded data. This latter function includes calibration and generation of the mix coefficients used to generate the mix channel. These coefficients are selected in a known way to eliminate in the mix channel, signals generated by fixed structures such as the support plates.

The data analysis function 67 includes eddy current analysis 75 of the plant data which will be discussed in detail below, a post processor 77 which correlates the indications generated by the eddy current analysis to the physical location within the steam generator, and generation of a preliminary report 79. The correlation performed by the post processor 77 is necessary because, as was discussed above, the data points are generated as a function of time, and due to variations in the speed with which the probe is pulled through the tube, the distance between data points can vary. This correlation is made by noting the data points at which indications of the support plates are generated and comparing those locations with the known physical locations of the indicated structural feature. The preliminary report 79 generates a list of all of the calls that were made by the analysis routine.

Figure 5:
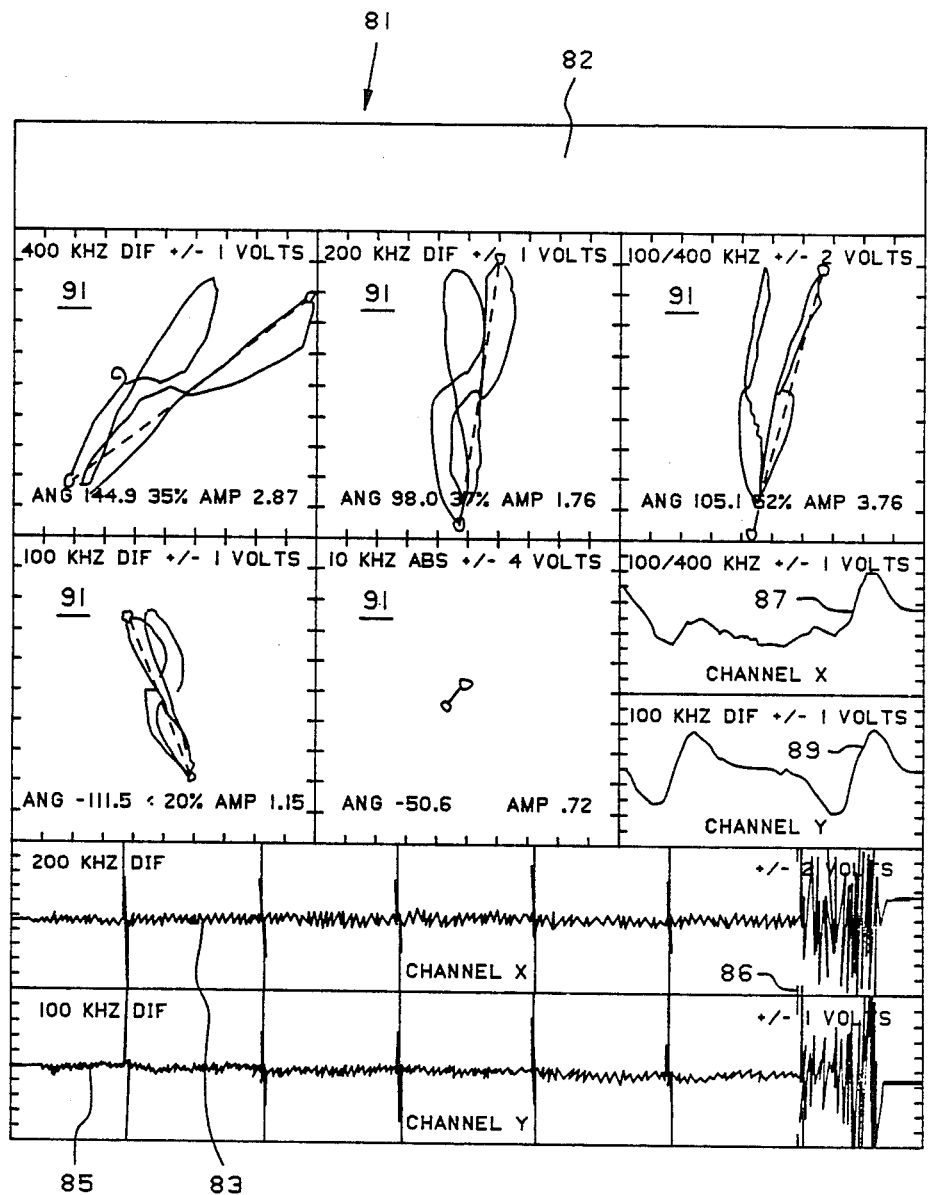
FIG. 5 is an example of a display generated by the apparatus of FIG. 3.

The human analyst can review the preliminary report and call up for graphic display 69 the strip chart data and lissajous figures for each call made by the data analysis program. An example of the graphical presentation available for the analyst is shown in FIG. 5. The display 81 presents general information (not shown) about the tube from which the displayed information was taken in a block 82 at the top. Across the bottom of the display 81 are two strip charts 83 and 85 which show one x component or channel of any operator selected frequency and one y component channel of any operator selected frequency, respectively, for the full length of the tube. The operator can zoom on any location along the tube with the cursor and the zoomed area of the strip chart, indicated by the zoom window marker 86, is shown in the two shorter strip charts 87 and 89 on the right of the display 81. Again, the channels for each of these strip charts are independently selectable by the operator. In the example, the larger strip charts are the 200 KHz differential x component, and the 100 KHz differential y component, while the shorter strip charts are the 100/400 KHz differential mix x component, and the 100 KHz differential y component.

The five remaining squares 91 in the graphic display 81 illustrate the lissajous patterns for each of the 4 frequencies and one mix channel of the area in the zoom window. The magnification of each of these can effectively be controlled from 0.5 volts to 256 volts. The maximum size and phase angle of each of the lissajou patterns is calculated, if desired, by simply pushing a button on the mouse 61. Capability is provided to zoom within the zoom window and repeat the process until it is possible to view the data only 1 point apart (for example at 30 mils axial distance in a typical field data set). The selection of calibration standard data segments for calibration and mixing can also be performed by the operator on the graphic screen using a simple sequence of push buttons on the mouse 61. The particular phenomenon shown in the exemplary display is a pair of flaws in the vicinity of the top of the tube sheet.

The human analyst can control the types of calls he wishes to review by deciding which categories are most important and calling for their display. After reviewing the selected displays the analyst can make any changes to the preliminary report he feels appropriate, including the leading calls.

File management 71 maintains records of the reels analyzed, the tubes analyzed and the results of the analysis. It also maintains the files for the raw data, mix and calibration files. The report output 73 generates a hard copy list of the "calls" or "indications" for each tube as modified from the preliminary report by the analyst.

Eddy Current Analysis

The analysis option of the system is implemented by a menu selection aid through the operator's terminal 47. The operator may direct that the analysis be performed in any one of three ways:

a. On all the data files currently stored on the unit or disk,
b. On all the data files associated with one instrument calibration, or
c. On one data file, which represents one tube.

The software that performs the analysis consists of the subroutines interfaced as shown in FIG. 6.

ECANL 93 is the main routine for running the eddy current analysis. It coordinates the data set-up required for the analysis by initializing variables and by calling the preanalysis routines. More particularly, the ECANL program proceeds generally as follows:

1. Initializes all variables and data arrays to their default values;
2. Obtains data from storage via call to READ4;
3. Determines the maximum and minimum values of the signal for each of the four frequencies;
4. Performs "mix" calculations and stores results, via call to COMPMIX;
5. Computes noise circle (ellipse) equation coefficients;
6. Determines initial average value signals via call to INITAVG4;
7. Locates all lobe excursions out of noise circle via call to ECAP4;
8. Compresses lobes into signals via call to COMPRESS4;
9. Breaks up overlapping signals in selected frequencies via call to BREAKUP.
10. Initiates analysis via call to ANALYZE4; and
11. Prints results of analysis via call to ECWRT.

The noise circle referred to in function 5 is a voltage threshold used to segregate eddy current signals from low-voltage noise. Through experience it has been found that voltage signals up to a particular magnitude and phase are often only low-voltage probe-wobble noise. Such a voltage threshold must be determined for each test frequency at each utility testing site. The voltage threshold can be thought of as a radius, so that a circle of this radius—a "noise" circle—would allow the evaluation of signals in any direction in the Vx-Vy plane. Only signals lying outside the noise circle are considered eddy current signals.

The nose circle is a convenient boundary for segregating eddy current signals from low-voltage probe-wobble noise because it can be defined by only two quantities, a center and a radius. A noise circle centered at (0,0) and having a noise radius of R is given by this equation:

$$X^2 + Y^2 = R^2 \qquad (1)$$

However, the principle noise source, probe-wobble, tends to be unidirectional. An ellipse, whose major axis is oriented in the direction of the wobble noise allows the noise circle concept to be extended so that high sensitivity at orientations divergent from the wobble can be achieved. Assuming that an ellipse has a horizontal axis of length "2a" (major axis) and a vertical axis of length "2b" (minor axis), the ellipse is defined by this equation:

$$X^2/a^2 + Y^2/b^2 = 1 \qquad (2)$$

Not all means of relating the two noise boundaries, however, are practical. Because the voltage origin drifts continuously in the Vx-Vy plane, changing the noise circle to a noise ellipse would require that a new ellipse equation be formulated for each new origin. With a noise circle, only the raidus is needed for signal segregation, which is constant regardless of the circle origin. Rather than discard the noise circle concept, the noise circle and probe-wobble ellipse are related to each other through a quantity called DEVSQ, the "squared deviation," given by this equation:

$$DEVSQ = X^2 + (a^2/b^2)Y^2 \qquad (3)$$

The expression for DEVSQ resembles a squared distance—the difference being the amplification of the Y component for an ellipse elongated in the x-direction. This amplification accounts for the fact that, for a probe-wobble ellipse the X and Y voltages are not equivalent. An eddy current signal exceeding the probe-wobble threshold in the Y-direction must be four times as great to exceed the threshold in the X-direction.

In equation (3), then, the Y voltage is amplified in an attempt to make the X and Y voltages compatible with the same noise radius for signal segregation.

During eddy current analysis, DEVSQ is calculated for each simultaneous pair of X and Y voltages. If DEVSQ is greater than the squared noise radius ($R^2$), the voltage signal is outside the noise circle and is, thus, considered an eddy current signal. Otherwise, it is considered probe-wobble noise.

The discussion so far has described only the base case for signal segregation. The base case no longer holds if the probe-wobble ellipse is rotated about its center in the Vx-Vy plane. This occurs naturally at certain test frequencies and also from faulty instrument calibration.

Therefore, a general form of equation (3) is needed for DEVSQ.

According to the principles of analytic geometry, if an XY-system is rotated through an angle "i" to obtain the X' Y'-system, then the coordinates of any fixed point are related by these equations:

$$X = X' \cos(i) - Y' \sin(i) \quad (4)$$

$$Y = X' \sin(i) + Y' \cos(i) \quad (5)$$

A zero degree angular displacement is defined as the major axis of the ellipse being parallel with the x-axis. (The ellipse is elongated in the x-direction.) An angular displacement "i" is defined as the arc traced between the positive major axis and positive x-axis in a counter-clockwise direction.

Substituting the new expressions for X and Y into equation (2) and regrouping the terms gives this equation for a rotated ellipse in the XY-plane:

$$a^2 = (X')^2[(a^2/b^2)\sin^2(i) + \cos^2(i)] + \quad (6)$$
$$X'Y'[2((a^2/b^2) - 1)\sin(i)\cos(i)] +$$
$$(Y')^2[\sin^2(i) + (a^2/b^2)\cos^2(i)]$$

X' and Y' are the x-component and y-component voltage changes with respect to the current origin. If "$a^2$" on the lefthand side is replaced with "DEVSQ", the resultant equation is the generalized equation for calculating DEVSQ for any rotated or non-rotated probe-wobble ellipse in the Vx-Vy plane. (Note that for i=0 degrees, equations (4), (5), and (6) reduce to equation (2).)

Equation 6 can be simplified with the substitutions in (7), (8), and (9) to give the general equation for DEVSQ, equation (10). The substititions are coefficients provided by the ECANL routine.

$$XMULT = (a^2/b^2)\sin^2(i) + \cos^2(i) \quad (7)$$

$$XYMUTL = 2(a^2/b^2 - 1)\sin(i)\cos(i) \quad (8)$$

$$YMULT = \sin^2(i) + (a^2/b^2)\cos^2(i) \quad (9)$$

$$DEVSQ = XMULT(X')^2 + XYMULT(X'Y') + YMULT(Y')^2 \quad (10)$$

Equation (10) is used for signal segregation in subroutine ECAP4 described below.

MIXRD subroutine 95 reads, from disk file 97, the mixing frequencies and mixing coefficients calculated as discussed in connection with the description of the data acquisition function 65.

The READ4 subroutine 99 copies of the unformated digitized eddy current data from a file on disk 97, modifies it and transfers it to an IDAT array which has nine channels: one for the absolute and differential signal for each of the four frequencies plus a mix frequency. Each channel includes an X and Y component of the associated signal.

The following are the principal signals used:
Frequency 1—400 KHz differential
Frequency 2—100 KHz differential
Frequency 3—10 KHz differential
Frequency 4—10 KHz absolute
An additional channel is reserved for the "mix" frequency data calculated later by the COMPMIX SUBROUTINE.

The COMPMIX subroutine 101 performs the mathematical mixing of two eddy current frequencies to generate the "mix" frequency, frequency 5. Frequency mixing is a means of cancelling or suppressing one of two superimposed signatures which have been produced at the same tube location. In eddy current inspection, the specific application of mixing is to "cancel" the tube support plate signatures and, thus, expose any superimposed tube defect signatures. These signatures are given such attention because tube defects may occur in the support plate crevice.

The mixing coefficients required by COMPMIX must be calculated before hand for every instrument calibration and are obtained through MIXRD subroutine 95. These coefficients provide a support plate and tube sheet signal suppression that is modeled in accordance with well known analog electronic mixer techniques. In the preferred embodiment, frequency 1 (400 KHz differential) and frequency 2 (100 KHz differential) data are mixed to generate frequency 5.

The INITAVG4 subroutine 103 calculates the initial X and Y voltage averages of the early eddy current data. Although the tube surroundings are assumed to be cylindrically symmetrical at the beginning of the data stream, an off-balance voltage is produced due to excessive noise. This results in displacement of the actual origin from (0,0) in the Vx-Vy plane. The INITAVG4 average is known as the "effective origin", and is calculated once per tube. It is initially calculated as the arithmetic average of the first 501 eddy current digital signals. If necessary, it is then adjusted downward for any point having an absolute value greater than 110 percent of the average. Such points are replaced with the arithmetic average in a re-averaging of the points, and the final average is the effective origin.

The ECAP4 subroutine 105 locates signal lobes in the Vx-Vy plane by determining which IDAT points are outside the noise "circle". To position the noise circle accurately for the calculations, the AVGSIG4 subroutine 107 is called to update the voltage average with each IDAT point examined. This updated average is the "current origin" in the Vx-Vy plane, and it replaces the effective origin calculated by the INITAVG4 subroutine 103. The noise circle which is calculated for each frequency in the manner discussed above in connection with the ECANL routine 93 is centered at the current origin.

The ECAP4 subroutine locates the points where the signal for each frequency leaves the nose circle and reenters the noise circle. The group of data points between the exit and re-entry points is identified as a lobe. The subroutine also identifies the location of the maximum signal in each lobe. The IDAT row pointers for the exit point, maximum point, and return point, for each lobe are stored in a LOCSIG array for the appropriate test frequency.

Before the ECAP4 subroutine 105 examines a new x-y pair of IDAT data, it calls the AVGSIG4 subroutine 107 to update the x and y voltage averages with these new values. The updated averages give the "current origin" in the Vx-Vy plane which replaces the effective origin calculated by INITAVG4. The need for updating the origin arises from the instability of eddy current inspection conditions. During probe travel through a tube, drifts in the electronic circuitry and slight variations in the tube wall dimensions produce a voltage drift, which causes the origin of the noise circle to migrate. Because eddy current signatures would be superimposed on this drift voltage, the drift voltage must be subtracted from the data before measuring signature features. The AVGSIG4 subroutine adjusts the average AVGSIG, between the 150th data point and the last data point in the data stream. The adjustment is accomplished by iteratively adding together a percentage of the "old average" and a complimentary percentage of the magnitude of the data point at the selected location. The present system utilizes 95% of the "old average" and 5% of the present signal. By incorporating only a small percentage of the new voltage into the average, the low-pass filtering achieved prevents voltage spikes from having a larger affect on the average voltage.

The COMPRESS4 subroutine 109 groups the signal lobes in each frequency located by the ECAP4 subroutine 105 into eddy current signatures. A signature is the complete set of signal lobes produced by a tube defect, support plate, or tube sheet and is represented graphically by the Y-channel versus X-channel plotting of the eddy current signals which forms a lissajous figure. A signature is identified by the exit point of its first lobe and the return point of its last lobe. These points are extracted from the LOCSIG array through a search algorithm. This search counts the IDAT points between adjacent lobes. A separation of less than 200 data points (approximately 6 inches of tube data) indicates that the lobes probably belong to the same signature. A larger separation indicates that the last lobe is probably the first of a new signature. As the search proceeds, the exit point of the first lobe and the return point of the last lobe of each signature are stored in an ISIG array as the exit and return points of the signatures.

FIG. 7 is an example of a signature which would be identified by the above procedure. Such a figure is generated by plotting a number of successive data points. The computer, however, cannot "see" such a pattern since it only looks at the data points serially one at a time. In FIG. 7, the origin 113 is the location of the average signal value as determined by INITAVG4 for the first 150 points of data and AVGSIG4 for subsequent points. The computer identifies the lobes by the point 117 at which the data goes out of the noise ellipse 115 and the point 119 at which it returns. If the number of points between the return point 119 of the first lobe and the exit point 123 of the second lobe are less than 200 data points apart, COMPRESS4 groups the lobes into a signature which is defined by the exit point 117 of the first lobe and the return point 127 of the second lobe 125.

The BREAKUP subroutine 128 is called after the COMPRESS4 routine has grouped the lobes in each frequency into signature to divide any 10 KHZ signatures which overlap more than one 100 KHz signature into two signatures each of which does not overlap more than one 100 KHz signature. This is done to prevent double counting of a signature later in the analysis procedure.

Once all of the signatures in all the frequencies have been identified, the ECANL routine 93 calls the ANALYZE4 subroutine 129. This subroutine selects the appropriate analysis route for an eddy current signature based upon the number of data points it contains and, if necessary, its amplitude.

If a frequency 2 signature contains more than 200 data points, it may be composed of more than one signature, which would make it too complex for immediate analysis. In this instance, the MULTCLAS4 subroutine 131 is called by the ANALYZE4 subroutine to extract the component signatures and call the appropriate analysis route for each one.

If a frequency 2 signature contains 200 data points or less, the frequency 3 amplitude (between the frequency 2 end points) determines which of two analysis routes should be called. The TSCLASS4 subroutine 133 and MIXCLASS4 subroutine 135, which comprise the first standard analysis route, are called if this amplitude is greater than approximately 0.2 volts. A signature of this amplitude may actually be a support plate or tube sheet signature superimposed or O.D. deposit.

The TSCLASS 4 subroutine 133 is called first to analyze the frequency 3 signature for support plate, tube sheet, tube end, and antivibration bar characteristics. This frequency is little affected by tube flaws and dents, thus, providing a means to learn their locations relative the steam generator structures. The primary purpose of this analysis route, however, is to call MIXCLASS4 to analyze for tube flaw and dent characteristics. This analysis is performed on the mix frequency. As explained before, support plate and tube sheet signals are suppressed in the mixed frequency—ideally they should be eliminated—to expose any tube flaw or dent signals present.

If a frequency 2 signature contains 200 data points or less and has a frequency 3 amplitude less than or equal to approximately 0.2 volts, the second standard analysis route, the FLAWCLAS4 subroutine 137 is called. For such a signature, there is effectively no accompanying frequency 3 signal, so that only the frequency 1 signature needs to be analyzed. Frequency 1 gives the most accurate representation of tube flaws.

In order to determine the amplitude of the frequency 1 tube signature, the ANALYZE4 subroutine calls the MAXIMUM4 subroutine 139. This subroutine determines the maximum tip-to-tip voltage across an eddy current signature. This quantity is the "maximum voltage amplitude" of the signature, and the two points defining it are the "signature endpoints". The maximum lobe points found earlier by the ECAP4 subroutine 105 cannot be assumed to be the signature end points as well. A maximum lobe point defines the maximum lobe amplitude with respect to the AVGSIG current origin. But the maximum amplitude defined by the signature endpoints is not required to pass through this origin. Therefore, its endpoints cannot be assumed to coincide with its maximum lobe points.

Figure 8B:
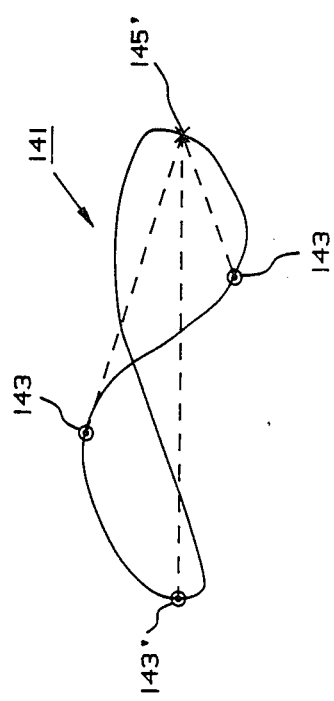

To determine signature end points, MAXIMUM4 converges upon them mathematically through the search algorithm depicted in FIGS. 8a and b. These Figures show a typical eddy current signature 141 as the lissajou figure resulting from X-channel versus Y-channel plotting of the signals. For the initial conditions of the search algorithm, the first point 143 in the signature range is temporarily set as one of the end points, say Endpoint 1, and the maximum squared amplitude is temporarily set to 0. The squared amplitude is then calculated from the temporary Endpoint 1, the "shooting point", to each of the other signature points, in sequence in search of Endpoint 2. Thus, these other signature points 145 are "projected" endpoints because each is considered a possible Endpoint. The projected Endpoint 145' giving the maximum squared amplitude with respect to Endpoint 1 is temporarily set as Endpoint 2 as shown in FIG. 8b. The squared amplitude is then measured from the temporary Endpoint 2 145, which is the new shooting point, to each of the other signature points, which again are projected Endpoints 143. The projected Endpoint 143' giving the maximum squared amplitude with respect to temporary Endpoint 2 is set as the new Endpoint 1. By alternating the shooting points as shown in FIG. 8, the algorithm will eventually converge upon the true Endpoints.

Once the maximum voltage amplitude and signature Endpoints have been determined, the SLOPE 4 subroutine 147 is called to calculate the phase angle of the maximum amplitude. The angle returned to the calling routine is measured counter-clockwise with respect to the positive x-axis, and is given in degrees between 0 degrees and 180 degrees.

When called by the ANALYZE4 subroutine, the TSCLASS4 subroutine 133 identifies the following steam generator structural component signatures at frequency 3:

1. Normal support plate
2. Distorted support plate
3. Normal tube sheet A (cold leg)
4. Distorted tube sheet A
5. Normal tube sheet B (hot leg)
6. Distorted tube sheet B
7. Antivibration bar (AVB)
8. Tube End In general, a normal support plate signature is characterized by a maximum voltage amplitude greater than about 4 volts and a phase angle between 70 degrees and 110 degrees. Otherwise, it is a distorted support plate signature if its amplitude is greater than about 1 volt, but less than 4 volts, its phase angle is less than 70 degrees but greater than 110 degrees, and it displays an absolute frequency voltage shift of less than 3 volts. This voltage shift is measured using values generated by the AVG50HIY4 and AVG50LOY4 subroutines 149 and 151 respectively discussed below.

In general, a tube sheet signature is characterized by a maximum voltage amplitude greater than about 1 volt and an absolute-frequency voltage shift exceeding 3 volts. A cold-leg tube sheet displays a voltage shift greater than 3 volts and a hot-leg tube sheet displays a shift of less than minus 3 volts. In addition to these criteria, if the tube sheet A or B is normal, it signature will have a phase angle between 70 degrees and 110 degrees after modification for the particular voltage shift. Otherwise the tube sheet is distorted. For a negative voltage shift the phase angle is modified to the angle traced by the Endpoint 2 to the last data point of the signature and for a positive voltage shift the phase angle is modified to the angle traced by the Endpoint 1 to the last data point.

In general, the TSCLASS4 subroutine identifies two different types of antivibration bars by analyzing the amplitudes of the signature in two separate channels. The specific criteria are described in connection with the description of the TSCLASS4 flow chart, FIG. 10, below.

The SIGSET subroutine 153 stores the information generated by the MAXIMUM4 subroutine 139 in a SIGNAL array. The following features of each signature are stored in the SIGNAL array: the exit point, the return point, the phase angle of the maximum voltage amplitude, the magnitude of the maximum voltage amplitude, a type identification code, Endpoint 1, and Endpoint 2, and the frequency, in its integer representation, at which the signature was identified. This array when completed contains the information which comprise the final results of the eddy current signature analysis.

The AVG50LOY4 and AVG50HIY4 subroutines 149 and 151 aid in the identification of support plate and tube sheet signatures. These routines provide the absolute-frequency voltage shift used as a test to distinguish between support plate, hot-leg tube sheet, cold-leg tube sheet signatures. These routines calculate the arithmetic average of the frequency 4 (10 KHz absolute), channel Y IDAT data in two 50 point ranges: 1 range before, and 1 after, the TSCLASS4 signature endpoints. The resultant averages are returned to the TSCLASS4 subroutine 133 as AVGLO based on the 50 consecutive points beginning with the hundredth point before the start point of the signature and AVGHI which is based on the fifty consecutive points beginning with the 51 point after the endpoint of the signature.

The FLAWINAVB subroutine 152 is called the TSCLASS4 to look for flaws at the antivibration bars. In general, a normal AVB signature is characterized by a maximum voltage amplitude greater than about 0.4 volts on the 10 KHz absolute channel. The search for a "flaw" in this same segment is further restricted to only those "30" data points which correspond to the fastest excursion of the signal in that signature around the maximum. The flaw is detected by analyzing that fast excursion segment in the frequency 5 (mix) channel. The entire signature is viewed as a possible composite signature of individual tube flaw signals as well as noise signals. These components signals are identified as portions of the AVB fast excursion segment exhibiting a smooth rate of change of amplitude between successive data points. Such portions are constructed piece by piece from subsegments of the fast excursion segment by forming small triangles from three data points and measuring the area of the triangle formed thereby. Subsegments associated with triangles having an area which is less than a certain threshold value are grouped into "extended" segments. The resulting signals are likely to be a mixture of single segment and multi-segment signals formed by both tube flaws and noise.

The next analysis step in the extraction of the maximum vertical signal which progresses in the direction of a "flaw" like signal by introducing phase angle and amplitude constraints to the extended segments. The vertical component of each of these segments is added together if the consecutive segments satisfy two conditions.

1. The angle of the segment is between 40 degrees and 160 degrees measured clockwise from the local "noise" phase of the signature;
2. The segments are less than 25 points apart. All the segments are regrouped in this manner and the maximum vertical signal is identified as an AVB flaw signal.

When the TSCLASS4 subroutine 133 is completed, the ANALYE4 subroutine 129 calls the MIXCLASS4 subroutine 135. This subroutine examines large amplitude signatures in the mix frequency, and classifies them as a flaw, a dent, inner diameter noise, a tube transition or noise which can be ignored, based upon phase angle, amplitude, and, in some instances, the width of the signal lobe and the direction of trace rotation. MIXCLASS4 first class MAXIMUM4 to determine the amplitude and angle of the mix frequency 5 signature based on frequency 2 entry and exit points. If the amplitude is greater than 20 volts, the signature could be a large dent, tube end or tube transition. If less than 20 volts it could be a residual of a tube support, a flaw, a small dent, or I.D. noise.

In the first case if the amplitude of frequency 5 is greater than 160 volts and the angle is greater than 15 degrees and less than 160 degrees then it is classified as a tube end. If the steam generator tube is not full depth expanded in the tube sheet then the tube end region is examined for flaws by SCANSLP4 subroutine. If frequency 5 amplitude is greater than 20 volts but less than 160 volts then the signature is tested for a transition region by using TRANSCLASS4 subroutine.

The signature previously tested by TRANSCLASS4 or the signature with an amplitude of less than 20 volts is compared with the results of TSCLASS4 to determine if the corresponding frequency 3 signature was a support plate. If it was then it is identified as a tube support residual. If it did not coincide with the support plate then the signature is tested by subroutine FLAWCHK. If the signal is a support residual then the associated frequency 1 angle is found. If frequency 1 angle is greater than 105 degrees and less than 155 degrees then the subroutine SCANSUPT is used to find any flaws contained in the residual. IF the frequency 1 angle is less than 105 degrees and greater than 155 degrees the signature is classfied as a distorted support plate. The signature is again tested by the FLAWCHK subroutine.

The SCANSUPT subroutine 154 is called by MIXCLASS4 to examine the possibility that a distorted mix channel residual signal may in fact be a flaw signal. If the corresponding maximum locations of the signals formed by the "assumed" flaw in frequency 5 and frequency 3 coincide within 6 data points, then the MIXLASS4 subroutine calls the SCANSUPT subroutine to check the frequency 1 signal between the maximum points of frequency 3. The entire signature is viewed as a possible composite signature of individual tube flaw signals as well as noise signals. These components signals are constructed piece by piece from successive subsegments of the designated segment of the signature using the same technique as described above in connection with FLAWINAVB. Again the resulting signals are likely to be a mixture of single segment and multisegment signals formed by both a tube flaw and noise.

The next analysis step is the extraction of the noise signal by introducing phase angle and amplitude constraints. A signal must be rotated more than 15 degrees from the X-axis, and its amplitude after 300 percent amplification of the Y-component must be larger than the appropriate noise circle radius to maintain tube flaw potential. These signals are further combined if they are in sequence and their phase angles are within 15 degrees of each other. And finally, if the rotation of this combined segment is counterclockwise, which is indicated by the Y-voltage of component Endpoint 1 being less than the Y-voltage component at Endpoint 2, the signal is indicated as a flaw.

The TRANSCLASS4 subroutine 156 is called by MIXCLASS4 to aid in the location of a transition which is the boundary between the expanded portion of the tube in the tube sheet and the remainder of the tube. The existence of a transition signal is identified in the MIXCLASS4 subroutine by finding the maximum points in the frequency 5 (mix) channel and frequency 6 (400 KHz ABS) channel in relation to the end of the interval. If these maximum points are within 40 points of the signal ends then the amplitude of the signals defined by the maximum point as one extremity and the nearest end of interval as the other extremity are calculated. If either of these amplitudes exceed 20 volts. The MIXCLASS4 subroutine calls TRANSCLASS4 subroutine. This subroutine further narrows down the exact position (single value) of the transition by locating the end which has the fastest rate of change. This location along with other information is then stored for the transition singal.

The FLAWCHK subroutines 155 determines whether the signature represents a flaw, mix residual, tube support residual, inner diameter flaw, or noise which can be ignored. A detailed discussion of the manner in which this is achieved is discussed in connection with FIG. 13. If FLAWCHK does not identify the signature as one of these, the direction of rotation of the trace is determined by comparing the Y channel magnitude of the first and second maximum points of the signature. If the Y Channel magnitude of the first maximum point is less than the Y channel of the magnitude second maximum point, signal trace rotation is counterclockwise and the signature is classified as a dent. If the signal trace is rotating clockwise, the signature is classified as inner diameter noise. The signature is further checked by the SIGWIDTH4 subroutine 157 which calculates the signature width perpendicular to the amplitude between ENDPOINTS. If the width is greater than one half the noise radius for the channel, the signature is considered large enough to be a composite signature and must be divided into signals for analysis. The SCANSLP4 subroutine 159 is called to perform this operation. If the signature width is less than or equal to one half the noise radius the signal is ignored.

The MAXSIGY4 subroutine 159 calculates the maximum Y components for use in determing the rotation of a signature.

The SCANSLP4 subroutine 159 analyzes a signature undergoing MIXCLASS4 analysis that cannot be identified as a tube end, and cannot at first glance be identified as a tube flaw. SCANSLP4 pursues the tube flaw analysis by viewing the signature as a possible composite signature of individual tube flaw signals as well as noise signals. These components signals are constructed piece by piece from signature segments three data points each. Segments are grouped into signals according to phase angle. Contribution of the smaller segments to the eddy current effect is considered insignificant. Segments in sequence and having phase angles within 15 degrees of each other are grouped into the same signal. The resulting signals are likely to be a mixture of single-segment and multi-segment signals formed by both tube flaws and noise.

The next analysis step is the extraction of the noise signals by introducing phase angle and amplitude constraints. A signal must be rotated more than 15 degrees from the x-axis, and its amplitude—after 300% amplification of the Y-component—must be larger than the appropriate noise circle radius to maintain tube flaw potential. And finally, if the rotation of the segment is counterclockwise, which is indicated by the Y-voltage component Endpoint 1 being less than the Y-voltage component at Endpoint 2, the signal is indicated as a flaw.

The ANALYZE4 subroutine 129 calls the FLAWCLAS4 subroutine 137 for analysis of signals having an amplitude of less than approximately 0.2 volts in frequency 3. The FLAWCLAS4 subroutine controls the passing of the signature to the FLAWCHK subroutine 155 for tube flaw analysis.

FLAWCLAS4 execution begins with a call to FLAWCHK for the frequency 1 signature. If it is not identified as a tube flaw based on frequency 1 characteristics, the frequency 2 characteristics are examined in a manner discussed in connection with FIG. 12.

The MULTCLAS4 subroutine 131 conducts the analysis of a frequency 2 signature containing more than 200 data points. The subroutine consists of three parts: Part 1 determines if any overlap occurs between the frequency 2 signature to be analyzed and the frequency 3 signatures. Overlap between the two frequencies indicates that any tube flaws, dents, or inner diameter noise present may be in the vicinity of support plates or tube sheets. The overlapping portions must be analyzed for support plates and tube sheets as well as tube flaws and dents. If no overlap occurs, the SCANLOBE4 subroutine 161 is called to analyze the signature. Part 2 of the MULTCLAS4 subroutine coordinates the calling of the appropriate analysis routines for the overlapping portions as follows:

A. If the frequency 3 signature contains less than 200 data points, TSCLASS4 and SCANMIX4 are called for the analysis.
B. If it contains 200 data points or more, it is divided into segments of up to 600 points. MAXIMUM4 is then called to determine if each segment is an appropriate size for analysis based on these factors:
  1. If the amplitude of a segment is approximately 1 volt or less, TSCLASS4 and SCANMIX4 are called.
  2. If the amplitude is greater than approximately 1 volt, and the second end point of the segment is within 20 points of Endpoint 2 of the frequency 3 signature, the segment is divided into smaller segments of 201 points each before calling TSCLASS4 and SCANMIX4.

Part 3 of MULTCLAS4 coordinates the calling of the appropriate analysis routines for the segments of the frequency 2 signature between the overlapping frequency 3 signatures. The segments are also known as "gaps". A segment containing at least 4 whole lobes is analyzed by the SCANLOBE4 subroutine 161. The more lobes the segment contains the more likely it is to be comprised of multiple signatures which SCANLOBE4 can determine. For segments containing fewer lobes, FLAWCLAS4 analysis is sufficient. Because these segments do not overlap with frequency 3 signatures, TSCLASS4 analysis is not required.

The SCANLOBE4 subroutine 161 segregates a MULTCLASS4 signature into its component signatures and passes them to FLAWCLAS4 for tube flaw analysis. However, SCANLOBE4 is called only for a MULTCLAS4 signature with no overlap between frequency 2 and frequency 3. The absence of such overlap indicates that the signature was not formed in the vicinity of the support plate or tube sheet and, therefore, does not require TSCLASS4 analysis.

The component signatures of the MULTCLAS4 signature are extracted by SCANLOBE4 by grouping its lobes according to their phase angles. A lobe phase angle, unlike a signature phase angle, is measured counter-clockwise from the positive x-axis to the line segment between the maximum lobe point and its current origin instead of the line segment between endpoints. To extract the component signatures, lobe 1 of the MULTCLAS4 signature is set as the first lobe, or base lobe, of the first component signature; similarly its phase angle is set as a base phase angle. Consecutive lobes immediately following the base lobe and having phase angles within 15 degrees of the base phase angle are grouped into the same signature. The exit and return points of the signature are saved.

When a lobe is encountered by the SCANLOBE4 subroutine that has a phase angle more than 15 degrees on the base phase angle it is recognized as the first lobe of a new signature. This lobe becomes the new base lobe—and its phase angle, the new base phase angle, for the new signature. The segregation continues for the remaining lobes of the MULTCLAS4 signature.

The SCANMIX4 subroutine 163 also segregates a MULTCLASS4 signature into its component signatures. It is identical to the SCANLOBE4 subroutine except that SCANLOBE4 analyzes frequency 1 data and passes the components signatures to FLAWCLAS4 subroutine 137 while SCANMIX analyzes the mix frequency, frequency 5, data and passes the components signatures to the MIXCLASS4 subroutine.

The POSTANAL subroutine 162 performs the task discussed earlier of correlating the position within the tube of the structural features determined from the time based eddy current data with the known physical location of such structures. The physical location of the defects, such as flaws, dents et cetera can then be determined relative to these known physical features. It also reclassifies certain indications bared upon the physical location of the call. For instance, an odd ball call is reclassified as tube sheet noise or tube noise depending upon where it occurred, and a dent call that matches probe wobble is reclassified as such.

The subroutine IGACLAS4 is called from subroutine ANALYZE4 after the tube support plate and tube sheet unique locations are identified. This subroutine looks for intergranular attack, or corrosion, in the unexpanded portion of tubes which are not full depth expanded in the tube sheet. The analysis interval for IGA detection is set 50 points inward on one end from the transition point, if one was detected by TRANSCLASS4, and 50 points inward from the top of the tube sheet on the other end. Alternatively, if no transition was detected that end of the interval is chosen as 150 points inward from the tube end. The corresponding frequency 7 signal (200 KHz absolute) in that interval is analyzed to locate the two maximum points and to determine the nature of the drift of that signal. Three types of IGA are identified based on positive drift, negative drift and nonuniform drift of the Y component of frequency 7 signal.

The ECWRT subroutine 165 constructs and prints the INSPECTION ANALYSIS RESULTS table. This table identifies such items as plant owner, unit and steam generator inspected, and inspection date. It also identifies the tube inspected, calibration log reference, mixing frequencies and coefficients, noise circle radii, and probe-wobble ellipse rotation angles, among other things. It also tabulates for each call, the data point at which the signature started and ended, the characterization of the signature, its phase angle and amplitude, the frequency at which the signature was recorded, the data points at which the maximums occurred and the value of the noise signal.

The PERFLAW subroutine 166 calculates the depth of penetration of each flaw based upon the phase angle of the signature and known curves stored in the computer which relate to depth of penetration.

The ASCFREQ subroutine 167 constructs a frequency identification character string to be written on the RESULTS ANALYSIS TABLE that is constructed and printed by the ECWRT subroutine.

Having described the individual subroutines, a more complete understanding of the invention can be realized from the description of the flow of the analysis process as set forth in the flow charts of FIGS. 9 through 13. FIG. 9 illustrates the flow chart of the ANALYZE4 subroutine 129, which controls the overall flow of the analysis program. As seen in block 169, if the frequency 2 signature, or compressed signal, is less than 200 data points long, the MAXIMUM4 subroutine 139 is called to determine the maximum amplitude of the signature using the frequency 2 limits and the frequency 3 data. If the frequency 3 amplitude is more than 0.2 of volts as determined in block 171, indicating that the signature probably represents a structure outside the tube, the TSCLASS4 subroutine 133 and the MIXCLASS4 subroutine 135 are called. If the frequency 3 amplitude is equal to or less then 0.2 volts than the FLAWCLAS4 subroutine 137 is called. On the other hand, if the signature under examination is more than 200 data points long, as determined in block 169, the MULTCLAS4 subroutine 131 is called to analyze for overlapping signatures. When all of the signatures have been analyzed by this process, the ANALYZE4 subroutine calls for a calculation of the steam generator structure as indicated in block 173 which then calls for the IGACLAS4 subroutine 175.

Figure 10B:
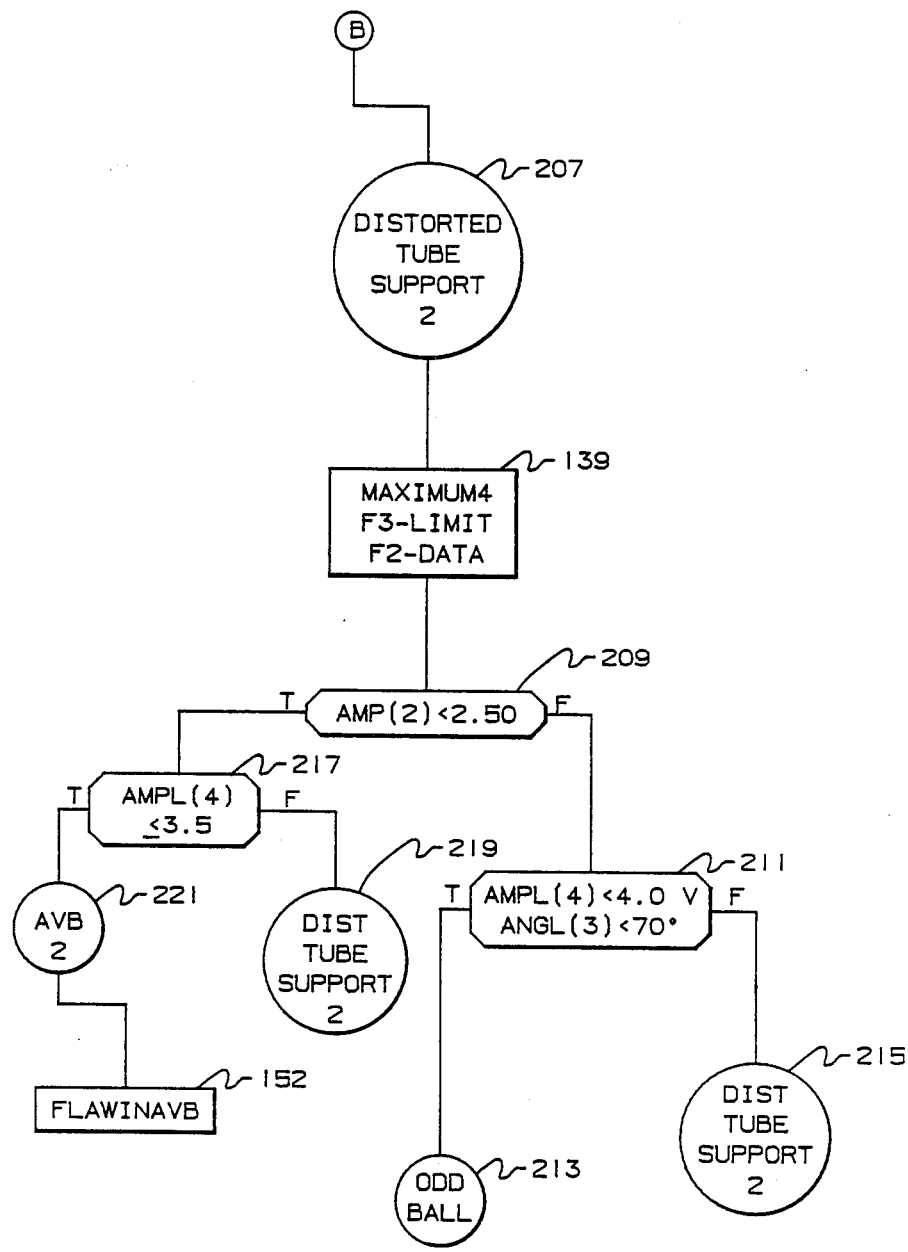
Figure 10C:
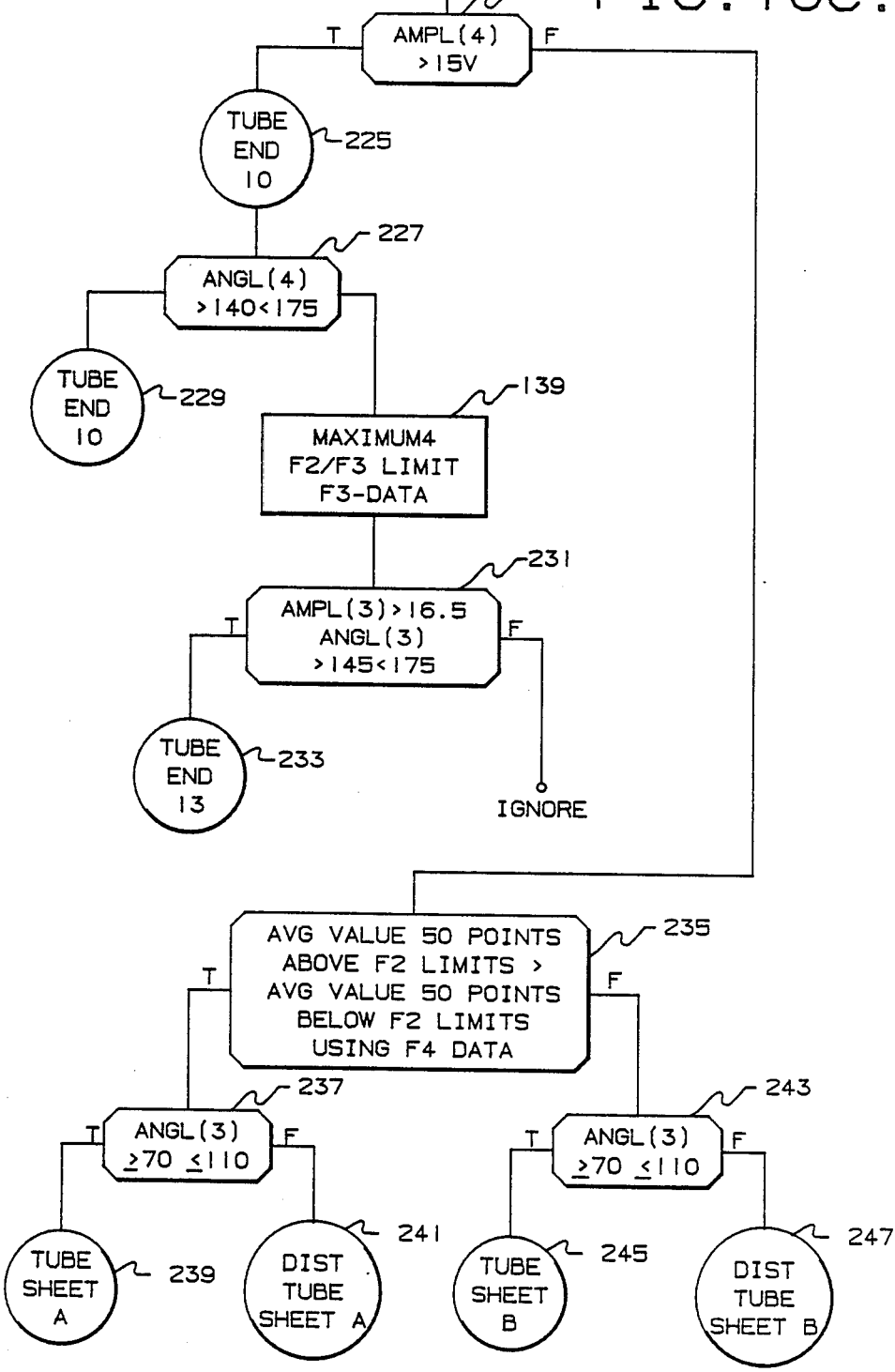
Figure 11B:
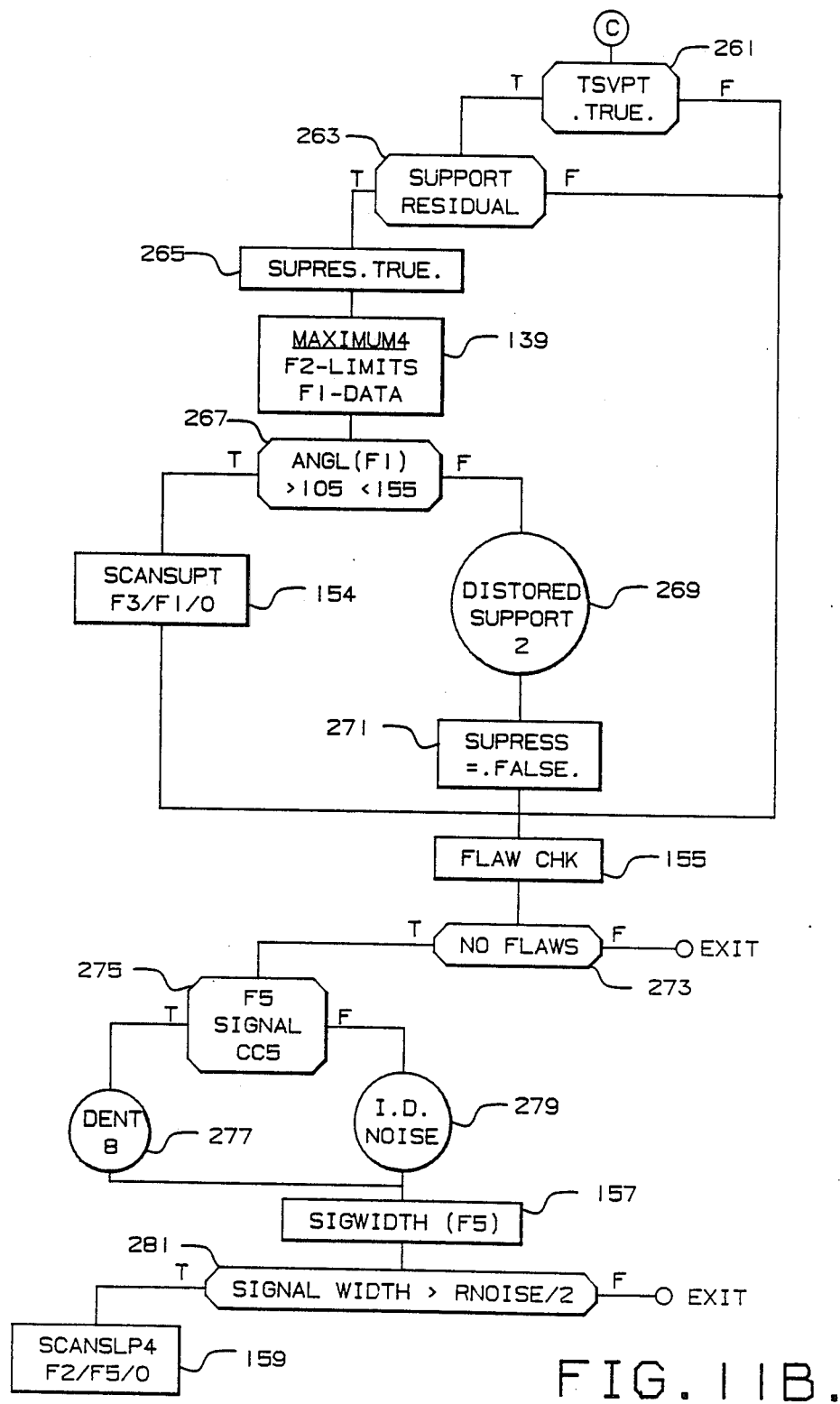

When called by the ANALYZE4 subroutine, the TSCLASS4 subroutine 133, which is illustrated in FIG. 10, sets in block 177 the internal TS flag to TRUE indicating that the structure is tube support like (i.e. either tube support or tube sheet) and sets the TSUPT flag FALSE indicating at this point that the signature has not yet been identified as a support plate. The MAXIMUM4 subroutine 139 is then called to determine the frequency 3 amplitude using the frequency 2 limits. The MAXIMUM4 subroutine calls the SLOPE4 subroutine 147 to determine the phase angle of the signature. If the frequency 3 amplitude is less than 1 volt as determined in block 179, then the MAXIMUM4 subroutine 139 is called again, this time using the frequency 4 data and the frequency 2 limits, to determine the frequency 4 amplitude. If the frequency 4 amplitude is more than 0.40 volts as determined in block 181, the signature is identified as an antivibration bar in block 183 and the FLAWINAVB subroutine is called as indicated by block 185 for further analysis of the signature to determine if a flaw might be present at the antivibration bar location. If the frequency 4 amplitude is less than 0.40 volts, the signature is identified as an "odd ball" in signal block 187. The "odd ball" designation in assigned to benign signatures which do not fit any of the known classification.

Returning to block 179, if the amplitude of the frequency 3 signal is more than 1 volt, the phase angle of the frequency 3 signature is examined in block 189. If this angle is between 70 and 110 degrees, and the amplitude is more than 4.40 volts as determined in block 191, TSFLAG is set to FALSE in block 193. In any event, the MAXSIGY4 subroutine 158 is called and, using the frequency 2 limits and the frequency 4 data, the absolute value of the 50 points before and after the frequency 2 limits of frequency 4 are calculated in the block 197. If the frequency 4 signal at these points is less than or equal to 3 volts and the frequency 3 amplitude is more than 4.4 volts, and its phase angle is between 70 and 110 degrees as determined by a check of the TSFLAG in block 199, then TSUPT is set to TRUE in block 201 and the signature is identified as a tube support in block 203. If the absolute values of the 50 points before and after the frequency 2 limits of the frequency 4 data are more than 3 volts but the amplitude of the frequency 3 signature is less than or equal to 17.60 volts as determined in block 205, or if TSFLAG was false in block 199, then the signature is temporarily characterized as a distorted tube support in 207. As a further check, MAXIMUM 4 is called using the frequency 3 limits to determine the amplitude of the frequency 2 signature. If the frequency 2 amplitude is more than 2.50 volts as determined in block 209, and the frequency 4 amplitude is less than 4 volts, while the frequency 3 angle is less than 70 degrees, as determined in block 211, then the signature is reclassified as an odd ball in block 213; otherwise it is confirmed as being a distorted tube sheet in block 215. If the amplitude of the frequency 2 data is less than 2.5 volts but the frequency 4 amplitude is more than 3.5 volts as determined in block 217 the signature is confirmed as a distorted tube support in block 219. However, if the amplitude of the frequency 4 signal is less than or equal to 3.5 volts, the signature is recharacterized as an antivibration bar in block 221 and the FLAWINAVB subroutine 152 is called for further analysis of the signature.

If the absolute values of the 50 points before and after the frequency 2 limits of the frequency 4 signal as determined in block 197 are more than 3 volts, indicating a large shift in signal level, the frequency 4 amplitude is checked in block 223. If this amplitude is more than 15 volts, the signature is identified as a tube end in block 225, however, this is verified by measuring the frequency 4 phase angle in block 227. If the angle is between 140 and 175 degrees, the signature is confirmed as a tube end as indicated in block 229, otherwise MAXIMUM 4 is called and using the frequency 2 and frequency 3 limits, the frequency 3 amplitude and phase angle are measured. If this amplitude is more than 16.5 volts and the angle is between 145 and 175 degrees, as indicated in block 231, the signature is confirmed as being a tube end in block 233; otherwise it is ignored as being an erroneous signal.

If the amplitude of the frequency 4 signal is less than 15 volts as determined in block 223, the average value of the 50 points above the frequency 2 limits is compared to those below in block 235 using the frequency 4 data. If the average value of the points above the limit exceed those below, and the frequency 3 phase angle is between 70 and 110 degrees as determined in block 237, the signature is characterized in block 239 as tube sheet A, at the inlet side of the tube. If the phase angle does not fall within these limits it is identified as a distorted tube sheet A in block 241. Similarly, if the average signal shifts in the opposite direction, the signature is identified as tube sheet B in block 245 is the frequency 3 phase angle is between 70 and 110 degrees as determined in block 243; otherwise it is identified as distorted tube sheet B in block 247.

Following analysis of the large amplitude signals by the TSCLASS4 subroutine 133, the ANALYZE4 subroutine 129 calls the MIXCLASS4 subroutine 135 to determine if there are any flaws or dents in conjunction with the large O. D. signal. As a first step, this subroutine sets JTRANS equal to 0 and SUPRES equal to FALSE in block 249 of FIG. 11. JTRANS is a flag which indicates to a called subroutine the type of analysis to be performed. If it has a value of 0 the subroutine is to check for flaws only. A value of 1 calls for dents only, and a value of −1 calls for flaws and dents. SUPRES is a flag which identifies a signature as a support residual signal if it is TRUE. Using the frequency 5, or mix data, with the frequency 2 limits, MIX-CLASS4 checks the amplitude of the mix frequency signal. If this amplitude is more than 160 volts as determined by blocks 251 and 253, and the phase angle of the signature is between 15 degrees and 160 degrees, it is identified as a tube end in block 255. However, if this is a tube without full depth expansion as determined in block 257, a further check is made to determine if there are any flaws or dents present. Full depth expansion means that the tube was expanded to the full height of the tube sheet. The change in diameter of the tube from the normal size to the expanded size generates a transition signal. For a tube with full depth expansion, the mix frequency amplitude is checked in block 259 using the frequency 2 limits at the maximum point. If this amplitude is more than 20 volts, TRANSCLASS is called to look for flaws (J=0). If the amplitude is less than 20 volts, SCANSLP4 is called to check the mix frequency for flaws.

Returning to block 253, if the amplitude of the mix frequency signature is below 160 volts, or the angle is not between 15 and 160 degrees, TRANSCLASS is called to check for dents only in the mix frequency. Following this, or if the amplitude of the mix frequency was less than 20 volts as determined in block 251, the TSUPT flag is checked in block 261. If this flag is TRUE, and the signature has been indentified as a support residual as determined in block 263 by checking that the flaw signal coincides with the support, SUPRES flag is set TRUE in block 265 and the frequency 1 phase angle using the frequency 2 limits is examined in block 267. If this angle is between 105 and 155 degrees, SCANSUPT is called to examine the frequency 3 and frequency 1 signals for flaws. If the frequency 1 signal is outside of these limits the signature is identified as a distorted support in block 269 and the SUPRESS flag is made FALSE in block 271.

Whether TSUPT was found to be TRUE or FALSE in block 261, the FLAWCHK subroutine 155 is called as a further check for flaws. If this routine finds no flaws as indicated in block 273, the MIXCLASS4 routine is exited. However, if a flaw is found further analysis is performed by determining the rotation of the frequency 5 signal in block 275. If the rotation is counter clockwise, the signal is characterized as a dent in block 276. If the rotation is clockwise, it is identified as inner diameter noise in block 279. In either event SIGWIDTH is called to analyze the frequency 5 signal. If the signal width is more than one half the noise radius, as determined in block 281, then SCANSLP4 is called to examine the frequency 5 signatures for flaws; using frequency 2 limits, otherwise the program is exited.

Figure 12:
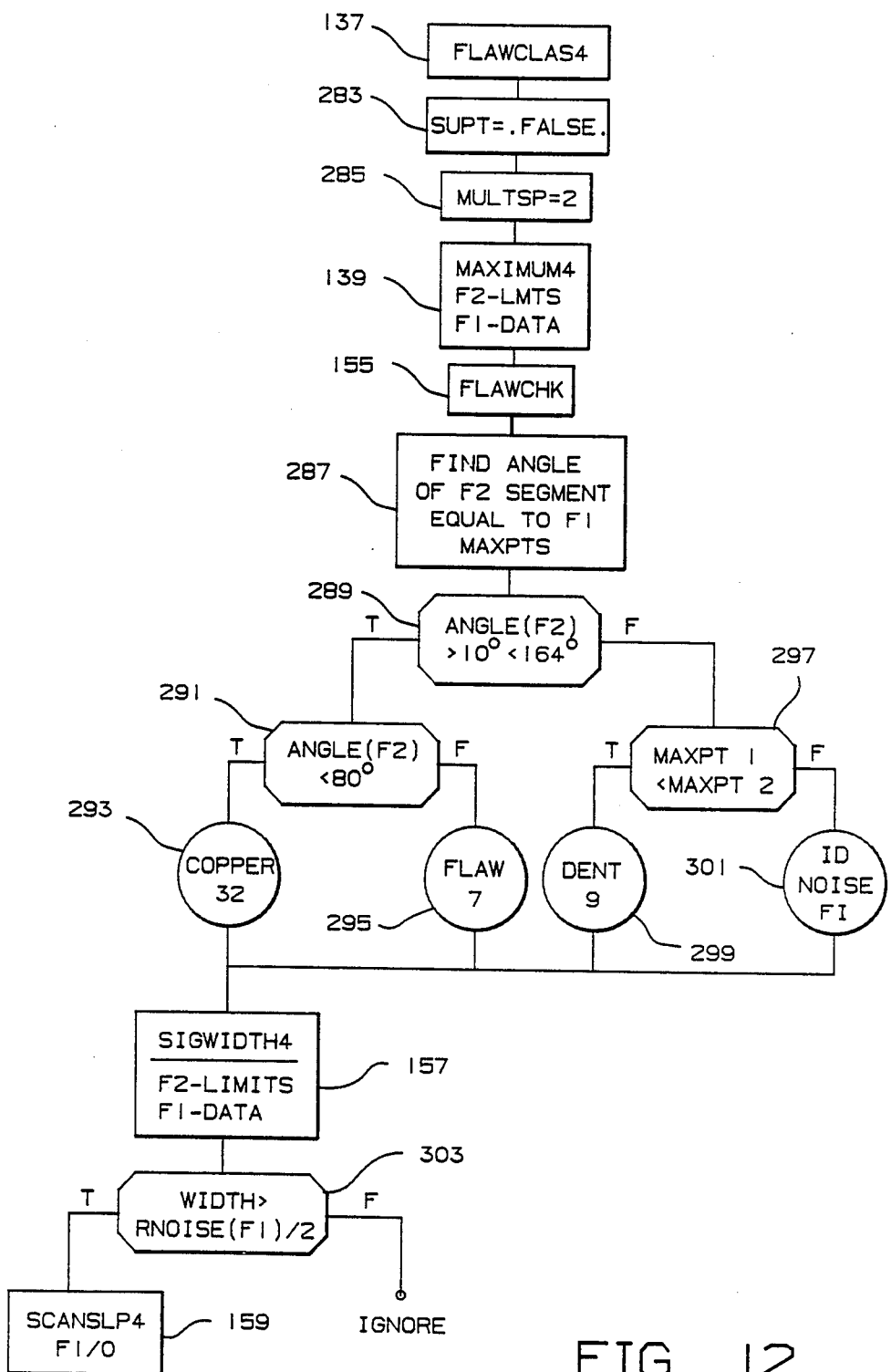
Figure 13:
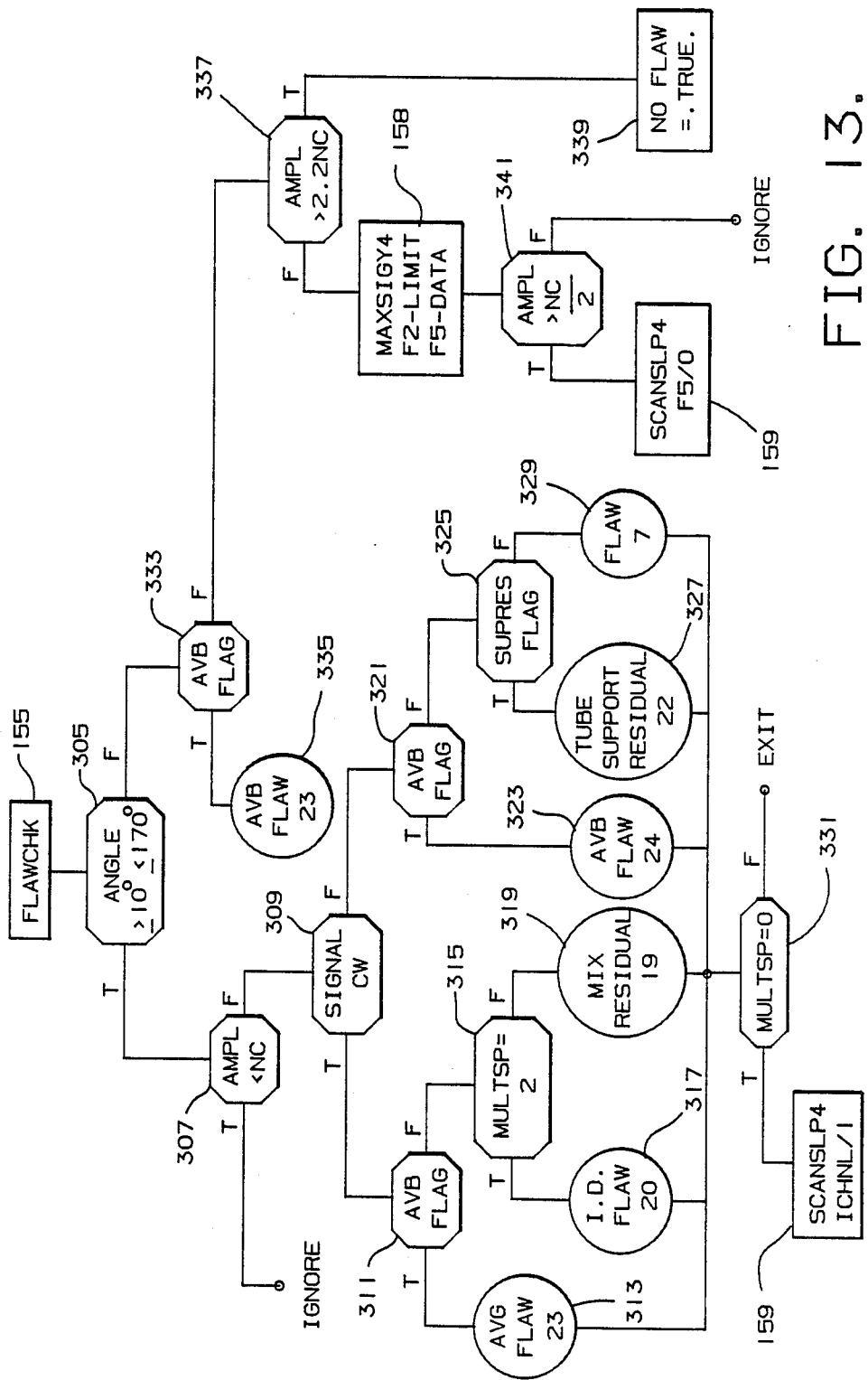
Figure 14:
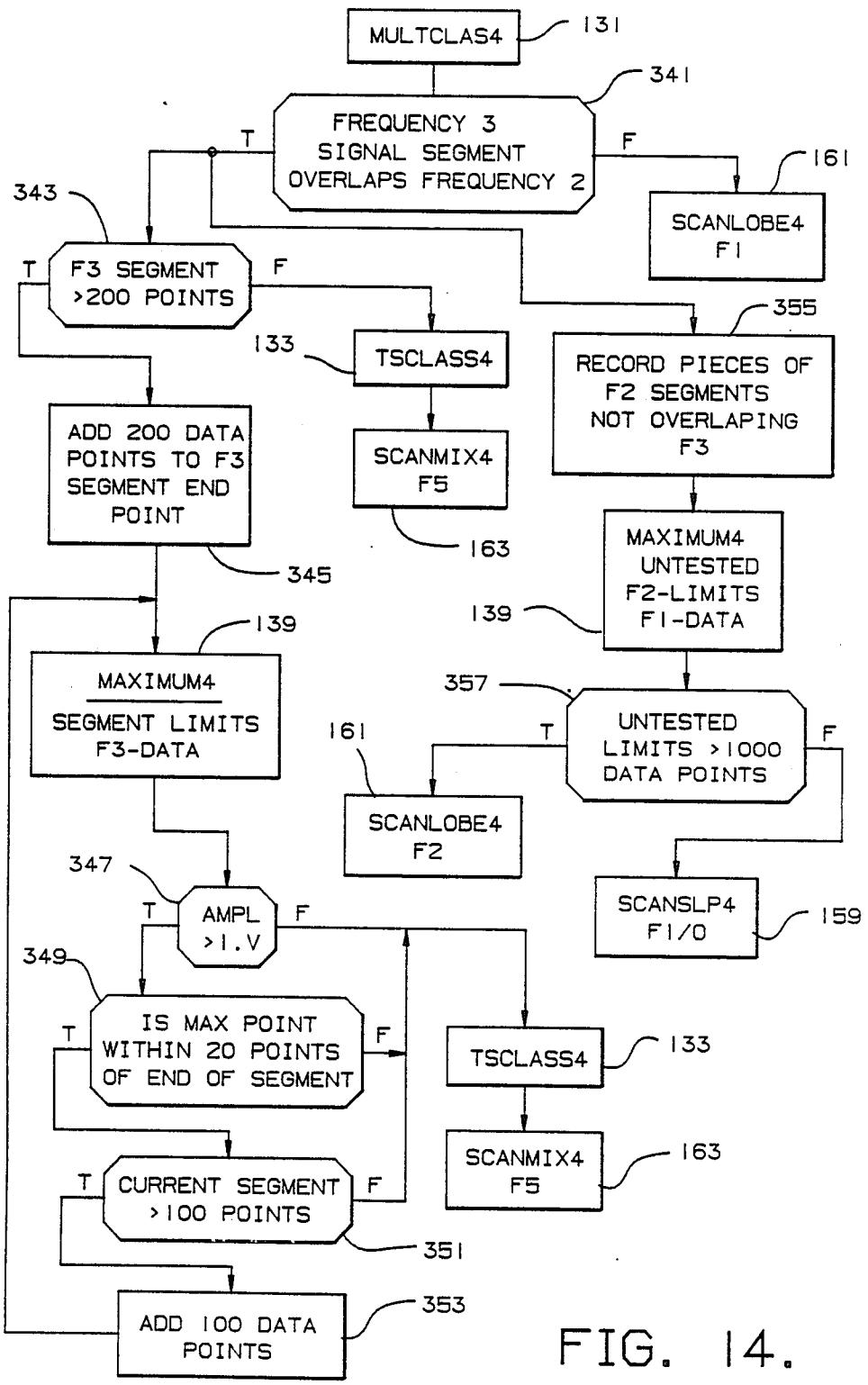

A flow chart of the FLAWCLAS4 subroutine 137, which is called by the ANALYZE4 subroutine 129 when the amplitude of the frequency 3 signal is less than 0.2 volts, is shown in FIG. 12. This subroutine begins by setting the TSUPT flag FALSE in block 283 and a MULTSP flag equal to 2 in block 285. The MULTSP flag indicates the conditions set by the calling routine. A "2" indicates that frequency 1 data should be used. The FLAWCHK subroutine 155 is then called using the frequency 1 data with frequency 2 limits. A flow cahrt of the FLAWCHK subroutine is shown in FIG. 13. If no flaws are detected by the FLAWCHK subroutine, the FLAWCLAS4 routine finds the angle of the frequency 2 segments equal to the frequency 1 max points in block 287. If this angle is between 10 and 164 degrees as determined in block 289, but is less than 80 degrees as determined in block 291, then the signature is identified as a copper deposit in block 293. If the angle is between 80 degrees and 164 degrees, it is identified as a flaw in block 295. If the frequency 2 angle is outside of 10 to 164 degrees and the rotation of the signature is counter clockwise, as determined in block 297, the signature is identified as a dent in block 299. On the other hand, if the rotation is clockwise, the signature is identified as inner diameter noise in block 301. For all of these characterizations, the SIGWIDTH4 subroutine 157 is called, and if the width of the signal is more than one half the amplitude of the frequency 1 noise threshold as determined in block 303, the SCANSLP4 routine 159 is called to check for flaws using the frequency 1 data. If the signal width does not exceed one half of the noise radius in block 303, the signature is ignored as noise.

The flow chart for the FLAWCHK subroutine 155 is shown in FIG. 13. This subroutine can be called by the FLAWCLAS4 subroutine 137 or the MIXCLASS4 subroutine 135 to determine the presence of flaws in the form of surface pits, holes, and cracks. It determines in block 305 the phase angle of the signature in the frequency requested by the calling routine, normally frequency 1. For angles of 10 degrees to 170 degrees, the amplitude is checked in block 307. Signatures with an amplitude less than that of the noise circle are ignored as noise. If the signature is outside the noise circle, the rotation of the signature is checked in block 309. If the rotation is clockwise, and the AVB flag is TRUE as determined in block 311 the signature is identified as a flaw at the antivibration bar in block 313. If the AVB flag is set to FALSE, the signature is identified as an inner diameter flaw in block 317 if the calling routine is examining the 400 KHz signal as determined in block 315, or a mix residual as shown in block 319 if the calling routine was analyzing the mix frequency (MULTSP=1).

If the rotation of the signature is counter clockwise as determined in block 309, and the AVB flag is TRUE as determined in block 321, a signature is recognized as a flaw at an antivibration bar at block 323. However, if the AVB flag is FALSE, but the SUPRES flag is TRUE as determined in block 325, the signature is identified as a tube support residual at 327 for counter clockwise rotation. With neither the AVB flag nor the SUPRES flag set TRUE, the signature is identified as a flaw at 329.

If the FLAWCHK subroutine was called by MIXCLASS4 sub-routine 135 (MULTSP=0) as determined block 331, then SCANSLP 4 subroutine 159 is called for a check for dents in the frequency (ICHNL) of the calling routine.

If the phase angle of the signature under examination is outside of the 10 degree to 170 degree range as indicated in block 305, but the AVB flag is set TRUE as determined in block 333, then the signature is identified as and AVB flaw at block 335. If the AVB flag is set FALSE, but the signal has an amplitude more than 220% of the noise circle as determined in block 337, then a NOFLAW flag is made equal to TRUE in block 339. For signals having a magnitude less than 220% of the noise circle amplitude, the frequency 5 Y component amplitude using the frequency 2 limits is checked by the MAXSIGY4 subroutine 158. If this amplitude is more than half the noise circle amplitude as determine in block 341, then SCANSLP4 is called to check the frequency 5 signature for flaws; otherwise the signal is ignored as noise.

Signatures found by the ANALYZE4 subroutine to be more than 200 data points long are broken down into their constituent signatures by the MULTCLAS4 subroutine 131. This subroutine is shown in FIG. 13. If the frequency 3 signal does not overlap the frequency 2 signal as determined in block 341, then the SCANLOBE4 subroutine 161, is called. SCANLOBE4 groups the lobes which are within plus or minus 15 degrees of each other into separate signatures for analysis by the FLAWCLASS subroutine 137.

The frequency 3 segments which overlap the frequency 2 signal are analyzed sequentially by first determining in block 343 whether the frequency 3 segment is more than 200 data points long. If it is not, it is analyzed by TSCLASS4 subroutine 133 which calls in turn SCANMIX4 subroutine 163. Frequency 3 segments which are more than 200 data points long are broken up into smaller segments of 200 data points each in block 345. The amplitude of the subsegment calculated by MAXIMUM4 139 is checked in block 347. If this amplitude is less than 1 volt, the subsegment is analyzed by the TSCLASS4 subroutine 133 followed by the SCANMIX4 subroutine 163. If the amplitude of the subsegment as determined in block 347 is more than 1 volt, a check is made in block 349 to determine if the end point of the subsegment is within 20 data points of the subsegment maximum amplitude point. If it is not, or even if it is but the subsegment is less than 100 data points long, as determined in block 351, subsegment is analyzed by TSCLASS4 and SCANMIX4 for flaw like characteristics. However, when the maximum point is within 20 points of the end of a subsegment which is more than 100 points long, an additional 100 points is added to the segment as indicated in block 353 and the extended subsegment is examined as a new subsegment. This procedure is followed because the arbitrary chopping of the frequency 3 segment into segments 200 data points long may result in including parts of 2 lobes in 1 segment.

When all of the frequency 3 segments have been analyzed the remaining pieces of the frequency 2 segments not overlapped by frequency 3 signals are recorded as indicated in block 355. MAXIMUM4 is then called using the untested frequency 2 limits and frequency 1 data. If an untested frequency 2 segment is more than 1000 data points long as determined in block 357, the frequency 1 signal is broken down into component signatures by SCANLOBE4; otherwise the frequency 1 signal is analyzed by SCANSLP4 for flaws.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of machine implemented analysis of eddy current test data recorded in quadrature channels at spaced data points as a probe is passed through the tubes of a heat exchanger, comprising the steps of:

storing the eddy current data for the spaced data points in a data array in a programmed digital computer;

operating the digital computer to examine the data in the array point by point to identify lobes;

operating the digital computer to group the lobes into signatures;

storing a set of rules in the digital computer for characterizing as a function of selected characteristics of said signatures, structural features surrounding the tubes and defects in the tubes; and operating the digital computer to apply said rules to said signatures to identify the structural features and defects and to generate an output identifying the structural features and defects identified.

2. The method of machine implemented analysis of claim 1 wherein said step of operating the digital computer to examine the data to identify lobes includes:

storing threshold values in the digital computer and operating the digital computer to sequentially point by point compare the data signals with the threshold values, and to identify as lobes the sequence of data points for which the amplitude of the data point signals exceed the threshold values.

3. The method of machine implemented analysis of claim 2 wherein said threshold values comprise quadrature components of a noise circle and wherein the comparing step comprises generating a data vector from the quadrature components of each data signal and comparing the magnitude of the data vector with a radius of the noise circle.

4. The method of machine implemented analysis of claim 3 including operating the digital computer to generate an average value of at least some of the data signals and to center the noise circle at said average value.

5. The method of machine implemented analysis of claim 4 wherein said average is a moving average comprising an initial average value of a selected number of data signals successively adjusted by the value of the data signal being examined.

6. The method of machine implemented analysis of claim 4 wherein a threshold factor weighted toward one axis is applied to the quadrature components of the eddy current data for each point for the comparison with the radius of the noise circle.

7. The method of machine implemented analysis of claim 2 wherein the step of operating the digital computer to group said lobes into signatures comprises operating the digital computer to count the number of data points between lobes and to group those lobes which are within a preselected number of data points from one another into a signature.

8. The method of machine implemented analysis of claim 7 further including the steps of operating the digital computer to count the number of data points in each signature, to break down signatures having more than a predetermined number of data points into component signatures and to apply said rules to said component signatures.

9. The method of machine implemented analysis of claim 8 wherein the step of breaking down a signature into component signatures comprises operating the digital computer to determine the phase angle of the lobes in said signature, and to group lobes having a predetermined phase angle relationship into a component signature.

10. The method of machine aided analysis of claim 9 wherein grouping lobes into component signatures comprise operating the digital computer to successively, beginning at one end of the signature, establish a first lobe as a base lobe, and to group all lobes having a phase angle within a prescribed number of degrees of a base lobe into a separate component signature.

11. The method of machine implemented analysis of claim 1 wherein at least some of said rules include evaluation of the phase angle of a signature and wherein the phase angle is calculated by operating the digital computer to determine the endpoints of the maximum amplitude of the signature and to measure the angle between a line joining the endpoints and a reference axis of the quadrature components.

12. The method of machine implemented analysis of claim 11 wherein the digital computer is operated to determine the endpoints of the maximum amplitude of the signature by selecting a data point as one endpoint and determining the other endpoint as the point which is the greatest distance in an X-Y plane of the quadrature components from said one endpoint, then determining a new position of the one endpoint by determining the point which is the farthest distance from said other endpoint and repeating the steps of determining new locations of the one and the other endpoints until the maximum distance between the one and the other endpoints is found.

13. A method of machine implemented analysis of multifrequency eddy current test data recorded in quadrature at spaced data points as a probe is passed through the tubes of a heat exchanger, said method comprising the steps of:
storing the multifrequency eddy current data for the spaced data points in a data array in a programmed digital computer; and
operating the digital computer to examine the data in the data array point by point to identify as lobes sequential data points which exceed preselected threshold values, to group lobes within a predetermined number of data points of each other into signatures, and as to each signature, to calculate the number of data points which define the signature, for signatures defined by less than a preselected number of data points to apply predefined rules to classify the signatures as one of a defined group of structural features, tube defects and irrelevant signals; and for a signature defined by more than said preselected number of data points to apply additional predefined criteria to break the signature down into component signatures and to then apply predefined rules thereto to classify each of the component signatures as one of a selected group of structural features tube defects and irrelevant signals.

14. The method of claim 13 wherein the step of operating the digital computer to apply additional predefined criteria to break down a signature defined by more than said preselected number of data points, includes calculating the phase angle of each of the lobes within such a signature, and grouping successive lobes within preselected phase angle ranges into component signatures.

15. The method of claim 14 wherein the step of operating the digital computer to break down signatures defined by more than said preselected number of data points includes operating the digital computer to identify segments of the signature in a first selected frequency of said multifrequency eddy current data which overlap segments of a signature in a second selected frequency, to apply said predefined rules to classify overlapping segments of the first frequency which are defined by less than a designated number of data points as one of a defined group of structural features, tube defects and irrelevant signals, to divide overlapping segments of the first frequency which are defined by more than said designated number of data points into subsegments of a preselected number of data points each, and to then apply said predefined rules to said overlapping subsegments to classify them as one of a defined group of structural features, tube defects and irrelevant signals.

16. The method of claim 15 wherein the step of dividing overlapping segments of the first frequency includes operating the digital computer to determine the maximum amplitude of the subsegment, to determine the number of data points between the data point at which said maximum amplitude occurs and the end of said subsegment, and to adjust the number of data points in said subsegment when the end of said subsegment is within a predetermined number of data points of the maximum point.

17. The method of claim 15 including the step of operating the digital computer to apply selected predefined rules to each of the segments of the signature in the second frequency which are not overlapped by segments of a first frequency signature to classify them as one of a group of tube defects and irrelevant signals.

18. The method of claim 17 including the step of prior to classifying the unoverlapped segments of the second frequency signature, to operate the digital computer to breakdown such segments having more than a given number of data points by grouping successive lobes in such a segment which are within a given number of degrees of each other into a component signature and then applying said certain predefined rules to the component signatures to classify them as representative of one of a designated group of structural features, tube defects and irrelevant signals.

19. The method of claim 13 wherein the step of applying predefined rules to a signature defined by less than a preselected number of data points includes; operating the digital computer: to calculate the amplitude of said signature, to apply predefined rules to classify a signature with an amplitude greater than a preset value as one of a designated group of structural features and irrelevant signals, and to apply predefined rules to classify a signature with an amplitude less than said preset value as one of a designated group of tube defects and irrelevant signals.

20. The method of claim 19 further including operating the digital computer to examine signatures classified as structural features point by point in selected regions to extract component signatures therefrom and to apply said predefined rules to said component signatures to classify them as one of a selected group of tube defects and irrelevant signals.

21. A machine implemented method of identifying from point by point eddy current test data recorded in quadrature, a flaw occurring in the vicinity of another feature which produces a larger signature than the flaw, comprising operating a digital computer to:
select as component portions of the larger signature successive data points over which the rate of change of amplitude of the signature is less than a predetermined value;

measure the phase angle and amplitude of said selected portions of the signature;

identify as representative of flaws those selected portions of the larger signature which meet preselected criteria including phase angle and amplitude.

22. The method of claim 21 in which eddy current data is recorded point by point in quadrature in several frequencies and wherein said digital computer is operated to:

identify the data point limits of the signature produced by said another feature using eddy current data recorded in a first frequency; and select said component portions of said larger signature in a second frequency only within the data point limits identified in said first frequency.

23. The method of claim 21 wherein the digital computer is further operated to determine the data point at which the maximum amplitude of said larger signature occurs, and to select component portions of said larger signal only within a predetermined number of data points of the data point at which the maximum amplitude occurs.

24. The method of claim 21 wherein said component portions of the larger signature are selected by operating the digital computer to:

construct piece by piece straight line segments extending between successive selected numbers of data points in said signature;

determine the phase angle of each of said segments; and group successive segments having phase angles within a predetermined number of degrees of each other into a selected portion of the signature.

25. The method of claim 21 wherein said component portions of the larger signal are selected by operating the digital computer to:

construct triangles from groups of three data points each;

determine the area of each of said triangles and compare the same with a threshold area; and group successive segments of the signature extending between data points forming said triangles having an area less than said threshold area into said selected portions of the signatures.

26. A method of eddy current testing for defects in tubes supported by support structures within a heat exchanger, comprising the steps of:

passing a probe through a tube and recording eddy current data signals for successive time spaced data points along the tube;

inputting the recorded eddy current data signals into a data file in a programmed digital computer;

programming into the digital computer a set of rules for analysis of the eddy current data to identify structural features of the heat exchanger and defects in the tubing;

operating the digital computer to analyze the eddy current data point by point and to apply said rules to identify structural features of the heat exchanger and defects in the tubes, if any;

inputting into the digital computer signals representative of the actual physical location of the structural features of the heat exchanger; and operating the digital computer to compare the physical location signals for the structural features with the data points at which said structural features were identified, and to thus, as a function of data points between the identified structural features and defects, generate an output identifying the locations of said defects in relation to the actual physical location of the structural features.

27. A machine implemented method of identifying flaws in the tubes of a heat exchanger from multifrequency point by point eddy current data gathered by passing a probe through the tubes; the method comprising the steps of:

inputting the multifrequency eddy current data into a digital computer;

operating the computer to examine the multifrequency data point by point to define as lobes sequential data points which exceed preselected threshold values and to group lobes within a preselected number of data points of the next lobe into signatures, to measure the amplitude, phase angle and direction of rotation of signatures in a first selected frequency and to identify as representative of a flaw a signature in said first frequency having an amplitude between preset limits, a phase angle of between about 10 to 15 degrees and about 165 to 170 degrees and a clockwise rotation.

28. A method of machine implemented analysis of eddy current test data recorded in quadrature at spaced data points, comprising the steps of:

storing the eddy current data for the spaced data points in an array in a digital computer;

operating the digital computer to establish a noise threshold as a function of selected quadrature components of the eddy current data;

operating the digital computer to point by point compare the eddy current data with said noise threshold and identified lobes as consecutive data points for which the value of the data points exceeds said noise threshold; and operating the digital computer to group the lobes into signatures.

29. The method of machine implemented analysis of claim 28 where in the step of operating the digital computer to group said lobes into signatures comprises operating the digital computer to count the number of data points between lobes and to group those lobes which are within a preselected number of data points from one other into a signature.

30. The method of machine implemented analysis of claim 29 further including the step of operating the digital computer to count the number of data points in each signature and to divide signatures having more than a predetermined number of data points into component signatures.

31. The method of machine implemented analysis of claim 30 wherein the step of dividing a signature into component signatures comprises operating the digital computer to determine the phase angle of the lobes in said signature, and to group lobes having a predetermined phase angle relationship into a component signature.

32. The method of machine aided analysis of claim 31 wherein grouping lobes into component signatures comprises operating the digital computer to successively, beginning at one end of the signature, establish a first lobe as a base lobe, and to group all lobes having a phase angle within a prescribed number of degrees of a base lobe into a separate component signature.

33. The method of machine implemented analysis of claim 30 wherein the eddy current test data is recorded in multiple frequencies and wherein the step of dividing signatures defined by more than said preselected number of data points includes operating the digital computer to identify segments of the signature in a first selected frequency of said multifrequency eddy current data which overlap segments of a signature in a second selected frequency, and to divide said overlapping segments of the first frequency which are define by more than a designated number of data points into subsegments of a preselected number of data points each.

34. The method of machine implemented analysis of claim 33 wherein the step of dividing overlapping segments of the first frequency includes operating the digital computer to determine the maximum amplitude of the subsegment, to determine the number of data points between the data point at which said maximum amplitude occurs and the end of the subsegment, and to adjust the number of data points in said subsegment when the end of said subsegment is within a predetermined number of data points of the maximum point.

35. The method of machine implemented analysis of claim 34 including the step of operating the digital computer to determine the number of data points in segments of the signature in the second frequency which are not overlapped by the signature in the first frequency, and to group successive lobes in a segment in the signature of the second frequency having more than a preselected number of data points which are within a given number of degrees of each other into a component signature.

36. The method of machine implemented analysis of claim 28 wherein the digital computer is operated to determine the end points of the maximum amplitude of a signature by selecting a data point as one endpoint and determining the other endpoint as the point which is the greatest distance in an X-Y plane of the quadrature components from said one endpoint, then determining a new position of the one endpoint by determining the point which is the farthest distance from said other endpoint and repeating the steps of determining new locations of the one and the other endpoints until the maximum distance between the one and the other endpoints is found.

37. Apparatus for analyzing a tube of a heat exchanger comprising:
 a probe and means for passing the probe through a tube to generate multifrequency point by point eddy current data in quadrature;
 means for storing said point by point eddy current data;
 means for electrically comparing said eddy current data point by point with threshold values to generate lobes, to group said lobes into signatures and to apply selected rules to said signatures to classify each of said signatures as one of a group of structural features, tube defects and irrelevant signals;
 means for generating a graphical display simultaneously depicting tube length strip charts of a quadrature channel of selected frequencies of data, zoom strip charts of a selected portion of the data in selected quadrature components of selected frequencies, and X-Y plane lissajous patterns of the selected portion of the data for multiple designated frequencies; and
 means for selecting said frequencies and said portions of the data.

38. Apparatus for analyzing point by point eddy current data recorded in quadrature from the tubes of a heat exchanger comprising:
 means for storing said data point by point as electrical signals;
 means for comparing said electrical data signals point by point with threshold signals and identifying as lobes sequences of data signals which exceed said threshold signals;
 means for grouping said lobes into signatures;
 means for applying preselected rules to said signatures to classify the same as one of a selected group of structural features, tube defects, and irrelevant signals; and
 means for generating an output identifying said classification of each signature.

* * * * *